(12) United States Patent
Wang

(10) Patent No.: US 9,695,161 B2
(45) Date of Patent: Jul. 4, 2017

(54) PRODRUGS OF AMINO QUINAZOLINE KINASE INHIBITOR

(71) Applicant: GlaxoSmithKline Intellectual Property Development Limited, Brentford, Middlesex (GB)

(72) Inventor: Gren Wang, Collegeville, PA (US)

(73) Assignee: GlaxoSmithKline Intellectual Property Development Limited (GB)

(*) Notice: Subject to any disclaimer, the term of this patent is extended or adjusted under 35 U.S.C. 154(b) by 0 days.

(21) Appl. No.: 15/080,969

(22) Filed: Mar. 25, 2016

(65) Prior Publication Data

US 2016/0207913 A1 Jul. 21, 2016

Related U.S. Application Data

(63) Continuation of application No. 14/397,218, filed as application No. PCT/US2013/059619 on Sep. 13, 2013.

(60) Provisional application No. 61/767,387, filed on Feb. 21, 2013, provisional application No. 61/700,422, filed on Sep. 13, 2012.

(51) Int. Cl.
  *C07D 417/12* (2006.01)
  *A61K 31/428* (2006.01)
  *A61K 31/517* (2006.01)
  *C07F 9/6561* (2006.01)

(52) U.S. Cl.
  CPC .......... *C07D 417/12* (2013.01); *A61K 31/428* (2013.01); *A61K 31/517* (2013.01); *C07F 9/6561* (2013.01)

(58) Field of Classification Search
  CPC .................................................. C07D 401/00
  See application file for complete search history.

(56) References Cited

U.S. PATENT DOCUMENTS

| | | | |
|---|---|---|---|
| 4,916,135 A | 4/1990 | Effland et al. |
| 5,457,105 A | 10/1995 | Barker |
| 5,576,322 A | 11/1996 | Takase et al. |
| 5,710,158 A | 1/1998 | Myers et al. |
| 5,801,180 A | 9/1998 | Takase et al. |
| 6,046,206 A | 4/2000 | Pamukcu et al. |
| 6,548,508 B2 | 4/2003 | Westbrook et al. |
| 6,589,758 B1 | 7/2003 | Zhu |
| 6,743,799 B2 | 6/2004 | Westbrook et al. |
| 6,809,097 B1 | 10/2004 | Thomas et al. |
| 7,282,504 B2 | 10/2007 | Armistead et al. |
| 7,452,887 B2 | 11/2008 | Dickson, Jr. et al. |
| 7,566,786 B2 | 7/2009 | Baldwin et al. |
| 7,569,577 B2 | 8/2009 | Hennequin et al. |
| 7,618,975 B2 | 11/2009 | Cai et al. |
| 7,709,479 B1 | 5/2010 | Mortlock et al. |
| 7,939,546 B2 | 5/2011 | Phiasivongsa et al. |
| 8,258,145 B2 | 9/2012 | Cai et al. |
| 9,216,965 B2 | 12/2015 | Casillas et al. |
| 2002/0026052 A1 | 2/2002 | Boschelli et al. |
| 2002/0147214 A1 | 10/2002 | Cockerill et al. |
| 2003/0087919 A1 | 5/2003 | Nagarathnam et al. |
| 2003/0105129 A1 | 6/2003 | Mortlock et al. |
| 2003/0125344 A1 | 7/2003 | Nagarathnam et al. |
| 2003/0212276 A1 | 11/2003 | Boschelli et al. |
| 2003/0216417 A1 | 11/2003 | Cumming |
| 2003/0220357 A1 | 11/2003 | Bankston et al. |
| 2004/0242604 A1 | 12/2004 | Bhattacharya et al. |
| 2005/0070561 A1 | 3/2005 | Jung et al. |
| 2005/0137395 A1 | 6/2005 | Hong et al. |
| 2005/0267101 A1 | 12/2005 | Randle |
| 2006/0025327 A1 | 2/2006 | Sanchez et al. |
| 2006/0116357 A1 | 6/2006 | Heron et al. |
| 2006/0167035 A1 | 7/2006 | Schwede et al. |
| 2007/0021446 A1 | 1/2007 | Ehlert et al. |
| 2007/0299092 A1 | 12/2007 | Floyd, Jr. et al. |
| 2008/0032996 A1 | 2/2008 | Mitsuya et al. |
| 2008/0045568 A1 | 2/2008 | Deng et al. |
| 2008/0064878 A1 | 3/2008 | Aoki et al. |

(Continued)

FOREIGN PATENT DOCUMENTS

| CN | 101362719 A | 2/2009 |
|---|---|---|
| EP | 0 973 746 B1 | 9/2003 |

(Continued)

OTHER PUBLICATIONS

Cavasotto, et al. Bioorg. & Med. Chem. Lett., 16: 1969-1974 (2006).

(Continued)

*Primary Examiner* — Paul V Ward
(74) *Attorney, Agent, or Firm* — Fang Qian

(57) ABSTRACT

Disclosed are compounds having the formula:

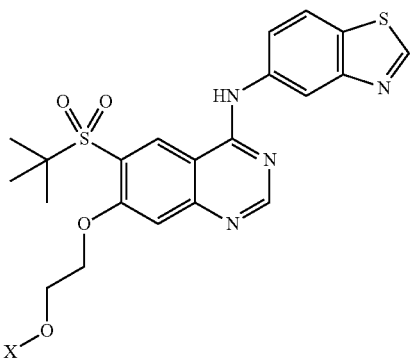

wherein X is as defined herein, and methods of making and using the same.

6 Claims, 4 Drawing Sheets

(56) References Cited

U.S. PATENT DOCUMENTS

| | | |
|---|---|---|
| 2008/0161305 A1 | 7/2008 | Forsyth et al. |
| 2008/0221132 A1 | 9/2008 | Cai et al. |
| 2008/0227811 A1 | 9/2008 | Chen |
| 2008/0227812 A1 | 9/2008 | Chen |
| 2008/0234267 A1 | 9/2008 | Lackey |
| 2008/0269404 A1 | 10/2008 | Paul et al. |
| 2008/0312273 A1 | 12/2008 | Hennequin |
| 2008/0318971 A1 | 12/2008 | Hewes |
| 2009/0099106 A1 | 4/2009 | Phiasivongsa et al. |
| 2009/0215770 A1 | 8/2009 | Jung et al. |
| 2009/0270450 A1 | 10/2009 | Dakin et al. |
| 2010/0069412 A1 | 3/2010 | Heron et al. |
| 2010/0135999 A1 | 6/2010 | Nazare et al. |
| 2011/0053935 A1 | 3/2011 | Folkes et al. |
| 2011/0237629 A1 | 9/2011 | Meibom et al. |
| 2011/0256092 A1 | 10/2011 | Phiasivongsa et al. |
| 2012/0041024 A1 | 2/2012 | Charnley et al. |
| 2012/0053183 A1 | 3/2012 | Russu et al. |
| 2012/0070413 A1 | 3/2012 | Kim et al. |
| 2012/0122923 A1 | 5/2012 | Cosledan et al. |
| 2012/0165321 A1 | 6/2012 | Adams et al. |
| 2012/0219522 A1 | 8/2012 | Xi |
| 2013/0018039 A1 | 1/2013 | Bodmer et al. |
| 2013/0023532 A1 | 1/2013 | Casillas et al. |
| 2013/0023534 A1 | 1/2013 | Casillas et al. |
| 2013/0053375 A1 | 2/2013 | Bury et al. |
| 2013/0345258 A1 | 12/2013 | Bury et al. |
| 2014/0100234 A1 | 4/2014 | Knight et al. |
| 2014/0155396 A1 | 6/2014 | Bannen et al. |
| 2014/0256949 A1 | 9/2014 | Casillas et al. |

FOREIGN PATENT DOCUMENTS

| | | |
|---|---|---|
| EP | 2 072 502 A1 | 6/2009 |
| GB | 2 345 486 A | 7/2000 |
| WO | WO 96/09294 A1 | 3/1996 |
| WO | WO 98/05647 A1 | 2/1998 |
| WO | WO 02/068394 A1 | 9/2002 |
| WO | WO 02/092571 A1 | 11/2002 |
| WO | WO 03/018022 A1 | 3/2003 |
| WO | WO 03/026666 A1 | 4/2003 |
| WO | WO 2004/037814 A1 | 5/2004 |
| WO | WO 2007/045987 A1 | 4/2007 |
| WO | WO 2008/033748 A2 | 3/2008 |
| WO | WO 2008/033749 A2 | 3/2008 |
| WO | WO 2008/119771 A2 | 10/2008 |
| WO | WO 2009/080200 A1 | 7/2009 |
| WO | WO 2011/011522 A2 | 1/2011 |
| WO | WO 2011/112588 A1 | 9/2011 |
| WO | WO 2011/112588 A2 | 9/2011 |
| WO | WO 2011/120025 A1 | 9/2011 |
| WO | WO 2011/120026 A1 | 9/2011 |
| WO | WO 2011/123609 A1 | 10/2011 |
| WO | WO 2011/140442 A1 | 11/2011 |
| WO | WO 2012/021580 A1 | 2/2012 |
| WO | WO 2012/122011 A2 | 9/2012 |
| WO | WO 2013/025958 A1 | 2/2013 |
| WO | WO 2014/043437 A1 | 3/2014 |
| WO | WO 2014/043446 A1 | 3/2014 |
| WO | WO 2014/128622 | 8/2014 |
| WO | WO 2014/128622 A1 | 8/2014 |

OTHER PUBLICATIONS

Kumar, et al. J. Clin. Oncol., 26: 1742-1751 (Apr. 1, 2008).
Manon, et al. J. Molec. Biol., 365: 160-174 (2007).
Robinett, et al. Bioorg. Med. Chem. Lett., 17: 5886-5893 (2007).
Argast, et al. Molec. & Cell. Biochem., (Kluwer Academic Pubs) 268(1-2): 129-140 (2005).
PCT International Preliminary Report on Patentability & PCT Written Opinion of the International Searching Authority, PCT/US11/35521, Aug. 9, 2011.
PCT International Preliminary Report on Patentability & PCT Written Opinion of the International Searching Authority, PCT/US11/47183, Dec. 30, 2011.
PCT International Preliminary Report on Patentability & PCT Written Opinion of the International Searching Authority, PCT/US12/27439, Jun. 7, 2012.
PCT International Preliminary Report on Patentability & PCT Written Opinion of the International Searching Authority, PCT/US12/51247, Oct. 23, 2012.
PCT International Preliminary Report on Patentability & PCT Written Opinion of the International Searching Authority, PCT/US13/59600, Jan. 29, 2014.
PCT International Preliminary Report on Patentability & PCT Written Opinion of the International Searching Authority, PCT/US13/59619, Jan. 29, 2014.
EP Supplementary Search Report for PCT/US11/030103, dated Sep. 23, 2013.
EP Supplementary Search Report for PCT/US11/030104, dated Sep. 17, 2013.
EP Supplementary Search Report for PCT/US11/35521, dated Oct. 23, 2013.
EP Supplementary Search Report for PCT/US11/47183, dated Dec. 17, 2013.
Sheth, et al. Archives of Biochemistry & Biophysics, 503: 191-201 (2010).
Arostegui, et al., Arthritis & Rheumatism, 56(11):3805-3813 (2007).
Biancheri, et al., Digestive and Liver Disease, Abstract, 45S:S71 (2013).
Body-Malapel, et al., Laboratory Investigation, 88:318-327 (2008).
Carreno, et al., Acta Ophthalmologica, Abstract, 2014.
Corridoni, et al., PNAS, 110(42):16999-17004 (2013).
Denou, et al., EMBO Molecular Medicine, 7(3):259-274 (2015).
Dharancy, et al., Gastroenterology, 138:1546-1556 (2010).
Du, et al., Kidney International, 84:265-276 (2013).
Ermann, et al., PNAS, E2559-E2566 (2014).
Ferrero-Miliani, et al., Clinical and Experimental Immunology, 147:227-235 (2006).
Foley, et al., Pediatric Rheumatology, 11 (Suppl. 1):A3 (2013).
Geddes, et al., Infection and Immunity, 78(12):5107-5115 (2010).
Goh, et al., The Journal of Immunology, 191:2691-2699 (2013).
Goncalves, et al., The Scandanavian Journal of Immunology, 73:428-435 (2011).
Hedegaard, et al., Plos One, 6(5):e20253 (2011).
Heinhuis, et al., Ann Rheum Dis, 69:1866-1872 (2009).
Hysi, et al., Human Molecular Genetics, 14(7):935-941 (2005).
Ikeda, et al., Arthritis Research & Therapy, 16:R89 (2014).
Jamontt, et al., Journal of Immunology, 190:2948-2958 (2013).
Jun, et al., Journal of Leukocyte Biology, 94:927-932 (2013).
Kruger, et al., European Society for Organ Transplantation, 20:600-607 (2007).
Kvarnhammar, et al., Plos One, 8(7):e68701 (2013).
Liu, et al., Journal of Biological Sciences, 11(5):525-535 (2015).
McGovern, et al., Human Molecular Genetics, 14(10):1245-1250 (2005).
Murias, et al., Pediatric Rheumatology, 12(Suppl. 1):P293 (2014).
Nachbur, et al., Nature Communications, 6:6442 (2015).
Natarajan, et al., Journal of Neuroimmunology, 265:51-60 (2013).
Oh, et al., Plos Pathogens, 9(5):e1003351 (2013).
Ospelt, et al., Arthritis & Rheumatism, 60(2):355-363 (2009).
Paim-Marque, et al., Pediatric Rheumatology, 12(Suppl. 1):P272 (2014).
Penack, et al., The Journal of Experimental Medicine, 206(10):2101-2110 (2009).
Peng, et al., International Immunopharmacology, 13:440-445 (2012).
Pillai, et al., Seminars in Ophthalmology, 28(5-6):327-332 (2013).
Plantinga, et al., Rheumatology, 52:806-814 (2013).
Rebane, et al., The Journal of Allergy & Clinical Immunology, 129:1297-1306 (2012).
Rosenzweig, et al., Arthritis & Rheumatism, 62(4):1051-1059 (2010).
Rosenzweig, et al., Inflammation Research, 60:705-714 2011).

(56) References Cited

OTHER PUBLICATIONS

Rosenzweig, et al., *Investigative Ophthalmology & Visual Science*, 50(4):1746-1753 (2009).
Rosenzweig, et al., *Investigative Ophthalmology & Visual Science*, 50(4):1739-1745 (2009).
Saha, et al., *Cell Host & Microbe*, 5:137-150 (2009).
Sfriso, et al., *Autoimmunity Reviews*, 12:44-51 (2012).
Shaw, et al., *Immunity*, 34:75-84 (2011).
Shigeoka, et al., *The Journal of Immunology*, 184:2297-2304 (2010).
Uehara, et al., *Diagnostic Pathology*, 4(23):1746 (2009).
Vieira, et al., *The Journal of Immunology*, 188:5116-5122 (2012).
Walsh, et al., *Cytokine & Growth Factor Reviews*, 24:91-104 (2013).
Wiken, et al., *The Journal of Clinical Immunology*, 29:78-89 (2009).
Yu, et al., *Plos One*, 6(8):e23855 (2011).
Zhou, et al., *Diabetes & Metabolism*, 38:538-543 (2012).
Cai, et al. Journal of Medicinal Chemistry, 53(5): 2000-2009 (2010).
EP Supplementary Search Report for PCT/US2012/027439, dated Dec. 16, 2014.
Amendment, U.S. Appl. No. 14/283,352, filed Apr. 7, 2015.
Amendment, U.S. Appl. No. 14/396,559, filed Apr. 7, 2015.
Amendment, U.S. Appl. No. 14/002,147, filed May 15, 2015.
Amendment, U.S. Appl. No. 13/696,603, filed Feb. 6, 2015.
Foley et al., Pediatric Rheumatology, 2013,11 (Suppl):A3 (published Nov. 8, 2013; presented 7th Congress of ISSAID, Lusanne, Switzerland May 22-26, 2013).
Poster: C.R. Hanning, AAI Annual Meeting, Pittsburgh PA (May 4, 2014).
Poster: B. J. Votta, et al., Keystone Symposia on Innate Immunity, Keystone, CO (Mar. 7, 2012).
EP Supplementary Search Report for PCT/US2012/051247,dated Feb. 18, 2015.
Amendment, U.S. Appl. No. 14/239,193, filed May 12, 2015.
Tigno-Aranjuez, Genes & Development, vol. 24, 2666-2677, 2010.
Amendment, U.S. Appl. No. 14/762,905, filed Jul. 23, 2015.
Amendment, U.S. Appl. No. 14/239,193, filed Nov. 30, 2015.
Amendment, U.S. Appl. No. 14/002,147, filed Dec. 4, 2015.
Amendment, U.S. Appl. No. 14/933,201, filed Nov. 19, 2015.
Amendment, U.S. Appl. No. 14/934,395, filed Nov. 19, 2015.

PRODRUGS OF AMINO QUINAZOLINE KINASE INHIBITOR

BACKGROUND OF THE INVENTION

Field of the Invention

The present invention relates to novel prodrugs of a quinazolyl amine that inhibits RIP2 kinase and methods of making and using the same. Specifically, the present invention relates to novel prodrugs of 2-((4-(benzo[d]thiazol-5-ylamino)-6-(tert-butylsulfonyl)quinazolin-7-yl)oxy)ethanol.

Background of the Invention

Receptor interacting protein-2 (RIP2) kinase, which is also referred to as CARD3, RICK, CARDIAK, or RIPK2, is a TKL family serine/threonine protein kinase involved in innate immune signaling. RIP2 kinase is composed of an N-terminal kinase domain and a C-terminal caspase-recruitment domain (CARD) linked via an intermediate (IM) region ((1998) *J. Biol. Chem.* 273, 12296-12300; (1998) *Current Biology* 8, 885-889; and (1998) *J. Biol. Chem.* 273, 16968-16975). The CARD domain of RIP2 kinase mediates interaction with other CARD-containing proteins, such as NOD1 and NOD2 ((2000) *J. Biol. Chem.* 275, 27823-27831 and (2001) *EMBO reports* 2, 736-742). NOD1 and NOD2 are cytoplasmic receptors which play a key role in innate immune surveillance. They recognize both gram positive and gram negative bacterial pathogens and are activated by specific peptidoglycan motifs, diaminopimelic acid (i.e., DAP) and muramyl dipeptide (MDP), respectively ((2007) *J Immunol* 178, 2380-2386).

Following activation, RIP2 kinase associates with NOD1 or NOD2 and appears to function principally as a molecular scaffold to bring together other kinases (TAK1, IKKα/β/γ) involved in NF-κB and mitogen-activated protein kinase activation ((2006) *Nature Reviews Immunology* 6, 9-20). RIP2 kinase undergoes a K63-linked polyubiquitination on lysine-209 which facilitates TAK1 recruitment ((2008) *EMBO Journal* 27, 373-383). This post-translational modification is required for signaling as mutation of this residue prevents NOD ½ mediated NF-kB activation. RIP2 kinase also undergoes autophosphorylation on serine-176, and possibly other residues ((2006) *Cellular Signalling* 18, 2223-2229). Studies using kinase dead mutants (K47A) and non-selective small molecule inhibitors have demonstrated that RIP2 kinase activity is important for regulating the stability of RIP2 kinase expression and signaling ((2007) *Biochem J* 404, 179-190 and (2009) *J. Biol. Chem.* 284, 19183-19188).

Dysregulation of RIP2-dependent signaling has been linked to autoinflammatory diseases. Gain-of-function mutations in the NACHT-domain of NOD2 cause Blau Syndrome, early-onset sarcoidosis, a pediatric granulomateous disease characterized by uveitis, dermatitis, and arthritis ((2001) *Nature Genetics* 29, 19-20; (2005) *Journal of Rheumatology* 32, 373-375; (2005) *Current Rheumatology Reports* 7, 427-433; (2005) *Blood* 105, 1195-1197; (2005) *European Journal of Human Genetics* 13, 742-747; (2006) *American Journal of Ophthalmology* 142, 1089-1092; (2006) *Arthritis & Rheumatism* 54, 3337-3344; (2009) *Arthritis & Rheumatism* 60, 1797-1803; and (2010) *Rheumatology* 49, 194-196). Mutations in the LRR-domain of NOD2 have been strongly linked to susceptibility to Crohn's Disease ((2002) *Am. J. Hum. Genet.* 70, 845-857; (2004) *European Journal of Human Genetics* 12, 206-212; (2008) *Mucosal Immunology* (2008) 1 (Suppl 1), S5-S9. 1, S5-S9; (2008) *Inflammatory Bowel Diseases* 14, 295-302; (2008) *Experimental Dermatology* 17, 1057-1058; (2008) *British Medical Bulletin* 87, 17-30; (2009) *Inflammatory Bowel Diseases* 15, 1145-1154 and (2009) *Microbes and Infection* 11, 912-918). Mutations in NOD1 have been associated with asthma ((2005) *Hum. Mol. Genet.* 14, 935-941) and early-onset and extraintestinal inflammatory bowel disease ((2005) *Hum. Mol. Genet.* 14, 1245-1250). Genetic and functional studies have also suggested a role for RIP2-dependent signaling in a variety of other granulomateous disorders, such as sarcoidosis ((2009) *Journal of Clinical Immunology* 29, 78-89 and (2006) *Sarcoidosis Vasculitis and Diffuse Lung Diseases* 23, 23-29) and Wegner's Granulomatosis ((2009) *Diagnostic Pathology* 4, 23).

A potent, selective, small molecule inhibitor of RIP2 kinase activity would block RIP2-dependent pro-inflammatory signaling and thereby provide a therapeutic benefit in autoinflammatory diseases characterized by increased and/or dysregulated RIP2 kinase activity. International Patent Application PCT/US2012/051247 (WO2013/025958) describes a series of quinazolyl amine compounds which are indicated as inhibitors of RIP2 kinase. Specifically disclosed in that application is the compound 2-((4-(benzo[d]thiazol-5-ylamino)-6-(tert-butyl sulfonyl)quinazolin-7-yl)oxy)ethanol.

As is known in the art, the bioavailability of compounds within a structural class is difficult to predict. Relatively minor structural modifications often have a large impact on the absorption of a compound, its blood level concentrations and/or its half-life. As a consequence, structurally related compounds that have very good in vitro potency may vary in therapeutic effectiveness. The viability of a putative medicinal agent may be attenuated by poor oral bioavailability.

Prodrugs are bioreversible derivatives of drug molecules that undergo an enzymatic and/or chemical transformation in vivo to release the active parent drug, which can then exert the desired pharmacological effect. In both drug discovery and development, prodrugs have become an established tool for improving physicochemical, biopharmaceutical, or pharmacokinetic properties of pharmacologically active agents. In certain cases, identification of an appropriate prodrug may be necessary in order to obtain an effective orally-administered therapeutic.

SUMMARY OF THE INVENTION

The invention is directed to quinazolyl amine compounds according to Formula (I):

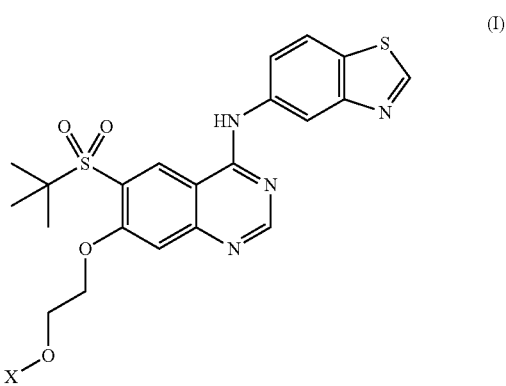

wherein:
X is selected from the group consisting of:

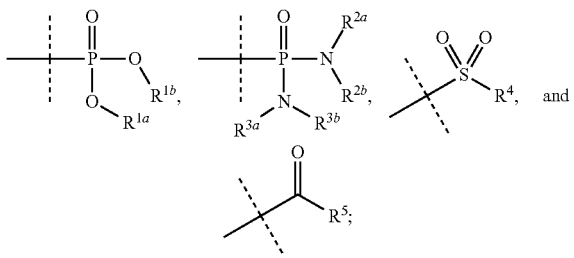

R$^{1a}$ and R$^{1b}$ are each independently H, (C$_1$-C$_4$)alkyl, or —CH$_2$OCO$_2$(C$_1$-C$_4$)alkyl;
or R$^{1a}$ and R$^{1b}$ together represent —(CH$_2$)$_2$— or —(CH$_2$)$_3$—;
R$^{2a}$, R$^{2b}$, R$^{3a}$, and R$^{3b}$ a are each independently H or (C$_1$-C$_4$)alkyl, wherein said (C$_1$-C$_4$)alkyl is optionally substituted by —CO$_2$(C$_1$-C$_4$)alkyl;
or R$^{2a}$ and R$^{2b}$ together represent —(CH$_2$)$_4$—, —(CH$_2$)$_5$—, —(CH$_2$)$_2$O(CH$_2$)$_2$—, —(CH$_2$)$_2$NH(CH$_2$)$_2$—, or —(CH$_2$)$_2$N(CH$_3$)(CH$_2$)$_2$—;
or R$^{3a}$ and R$^{3b}$ together represent —(CH$_2$)$_4$—, —(CH$_2$)$_5$—, —(CH$_2$)$_2$O(CH$_2$)$_2$—, —(CH$_2$)$_2$NH(CH$_2$)$_2$—, or —(CH$_2$)$_2$N(CH$_3$)(CH$_2$)$_2$—;
or R$^{2b}$ and R$^{3b}$ together represent —(CH$_2$)$_2$— or —(CH$_2$)$_3$—;
R$^4$ is —OH or —NH$_2$;
R$^5$ is (C$_1$-C$_6$)alkyl, —O(C$_1$-C$_4$)alkyl, —NR$^6$R$^7$, or 5- or 6-membered heterocycloalkyl, wherein said (C$_1$-C$_6$)alkyl is substituted by —OH, —OP(=O)(OH)$_2$, —NH$_2$, or —NHCO(C$_1$-C$_4$)alkyl, wherein the (C$_1$-C$_4$)alkyl group of said —NHCO(C$_1$-C$_4$)alkyl is optionally substituted by —NH$_2$, and wherein said 5- or 6-membered heterocycloalkyl is optionally substituted, one or two times independently, by (C$_1$-C$_4$)alkyl, oxo, or an additional 5- or 6-membered heterocycloalkyl; and
R$^6$ and R$^7$ are each independently H or (C$_1$-C$_4$)alkyl;
or a salt thereof The compounds according to Formula (I), or salts, particularly pharmaceutically acceptable salts, thereof, are upon administration to a host, converted into an inhibitor of RIP2 kinase. This invention is particularly directed to quinazolyl amine compounds according to Formula (I), or a salt thereof, particularly a pharmaceutically acceptable salt thereof, or a hydrate thereof, which, upon administration to a host, are converted into an inhibitor of RIP2 kinase.

Accordingly, the present invention is also directed to a method of inhibiting RIP2 kinase which method comprises administering to a host a compound according to Formula (I), or a salt, particularly a pharmaceutically acceptable salt, thereof.

The invention is further directed to a method of treating a RIP2 kinase-mediated disease or disorder which comprises administering a therapeutically effective amount of a compound according to Formula (I), or a salt, particularly a pharmaceutically acceptable salt thereof, to a patient (a human or other mammal, particularly, a human) in need thereof. Examples of RIP2 kinase-mediated diseases or disorders include uveitis, Crohn's disease, ulcerative colitis, early-onset and extraintestinal inflammatory bowel disease and granulomateous disorders, such as sarcoidosis, Blau syndrome, early-onset sarcoidosis and Wegner's Granulomatosis.

The present invention is further directed to a pharmaceutical composition comprising a compound according to Formula (I), or a salt, particularly a pharmaceutically acceptable salt, thereof and a pharmaceutically acceptable excipient. Particularly, this invention is directed to a pharmaceutical composition for the treatment of a RIP2 kinase-mediated disease or disorder, where the composition comprises a compound according to Formula (I), or a salt, particularly a pharmaceutically acceptable salt, thereof and a pharmaceutically acceptable excipient.

DETAILED DESCRIPTION OF THE INVENTION

Figure 1:
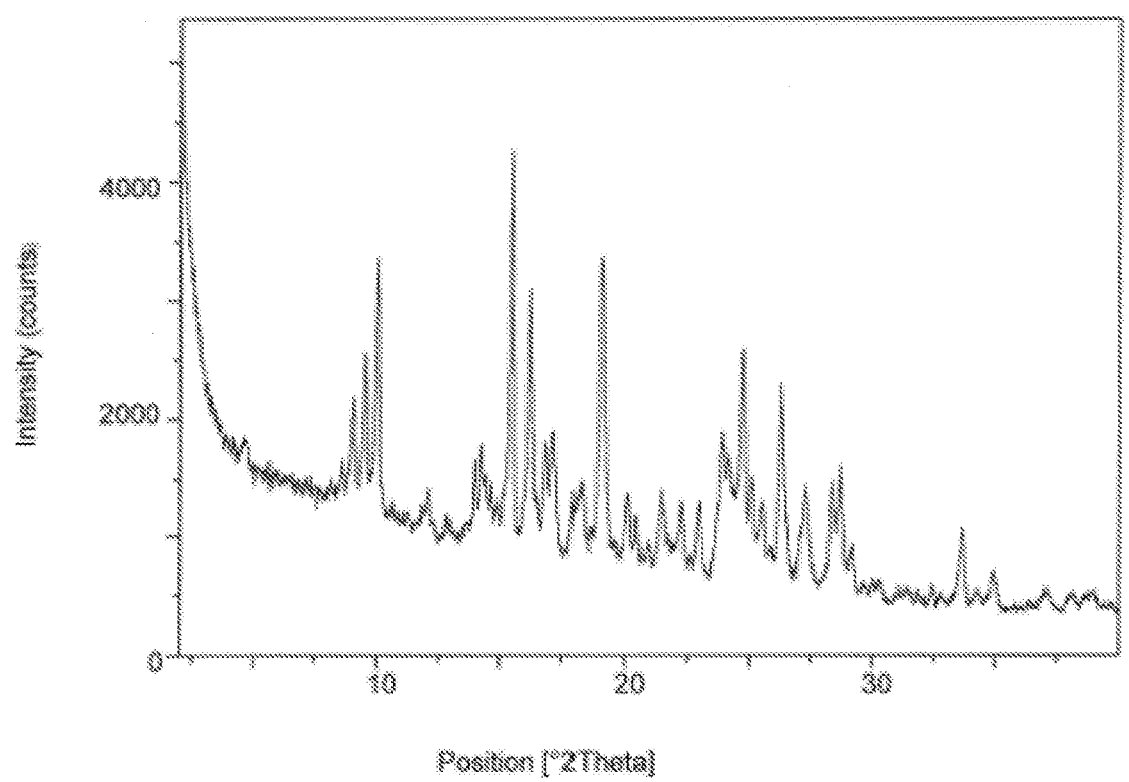
FIG. 1 is a powder x-ray powder diffraction (PXRD) pattern of a crystalline form of calcium (I) 2-((4-(benzo[d]thiazol-5-ylamino)-6-(tert-butylsulfonyl)quinazolin-7-yl)oxy)ethyl hydrogen phosphate trihydrate.

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

In addition, it will be appreciated by those skilled in the art that the compounds of this invention, depending on further substitution, may exist in other tautomeric forms. All tautomeric forms of the compounds described herein are intended to be encompassed within the scope of the present invention. It is to be understood that any reference to a named compound of this invention is intended to encompass all tautomers of the named compound and any mixtures of tautomers of the named compound.

As used herein, the term "alkyl" represents a saturated, straight or branched hydrocarbon moiety. Exemplary alkyls include, but are not limited to methyl (Me), ethyl (Et), n-propyl, isopropyl, n-butyl, s-butyl, isobutyl, t-butyl and pentyl. The term "C$_1$-C$_4$ alkyl" refers to an alkyl group or moiety containing from 1 to 4 carbon atoms.

"5- or 6-Membered heterocycloalkyl" represents a group or moiety comprising a non-aromatic, monocyclic radical, which is saturated or partially unsaturated, containing 5 to 6 ring atoms, which includes 1 to 4 heteroatoms selected from nitrogen, oxygen and sulfur. Illustrative examples of heterocycloalkyls include, but are not limited to, pyrrolidyl (or pyrrolidinyl), piperidinyl, piperazinyl, morpholinyl, tetrahydro-2H-1,4-thiazinyl, tetrahydrofuryl (or tetrahydrofuranyl), dihydrofuryl, oxazolinyl, thiazolinyl, pyrazolinyl, tetrahydropyranyl, dihydropyranyl, 1,3-dioxolanyl, 1,3-dioxanyl, 1,4-dioxanyl, 1,3-oxathiolanyl, 1,3-oxathianyl, and 1,3-dithianyl.

Heterocycloalkyl groups include 5-membered heterocycloalkyl groups containing one heteroatom selected from nitrogen, oxygen and sulfur and optionally containing one or two additional nitrogen atoms, or optionally containing one additional oxygen or sulfur atom, such as pyrrolidyl (or pyrrolidinyl), tetrahydrofuryl (or tetrahydrofuranyl), tetrahydrothienyl, dihydrofuryl, oxazolinyl, thiazolinyl, imidazolinyl, pyrazolinyl, 1,3-dioxolanyl, and 1,3-oxathiolan-2-on-yl.

Heterocycloalkyl groups are 6-membered heterocycloalkyl groups containing one heteroatom selected from nitrogen, oxygen and sulfur and optionally containing one or two additional nitrogen atoms or one additional oxygen or sulfur atom, such as piperidyl (or piperidinyl), piperazinyl, morpholinyl, thiomorpholinyl, 1,1dioxoido-thiomorpholin-4-yl, tetrahydropyranyl, dihydropyranyl, tetrahydro-2H-1,4-thiazinyl, 1,4-dioxanyl, 1,3-oxathianyl, and 1,3-dithianyl.

It is to be understood that the term heterocycloalkyl is intended to encompass stable heterocyclic groups where a ring nitrogen heteroatom is optionally oxidized (e.g., heterocyclic groups containing an N-oxide) or where a ring sulfur heteroatom is optionally oxidized (e.g., heterocyclic groups containing sulfones or sulfoxide moieties, such as tetrahydrothienyl-1-oxide (a tetrahydrothienyl sulfoxide) or tetrahydrothienyl-1,1-dioxide (a tetrahydrothienyl sulfone)).

"Oxo" represents a double-bonded oxygen moiety; for example, if attached directly to a carbon atom forms a carbonyl moiety (C=O).

As used herein, the terms "compound(s) of the invention" or "compound(s) of this invention" mean a compound of Formula (I), as defined above, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di-, tri- and hemi-hydrates)), and mixtures of various forms (various hydrates of a salt form).

As used herein, the term "optionally substituted" indicates that a group (such as an alkyl or heterocycloalkyl group) or ring or moiety may be unsubstituted, or the group, ring or moiety may be substituted with one or more substituent(s) as defined. In the case where groups may be selected from a number of alternative groups, the selected groups may be the same or different.

The term "independently" means that where more than one substituent is selected from a number of possible substituents, those substituents may be the same or different.

In addition, it will be appreciated by those skilled in the art that the compounds of this invention, depending on further substitution, may exist in other tautomeric forms. All tautomeric forms of the compounds described herein are intended to be encompassed within the scope of the present invention. It is to be understood that any reference to a named compound of this invention is intended to encompass all tautomers of the named compound and any mixtures of tautomers of the named compound.

In one embodiment of the compounds of Formula (I) of this invention, X is

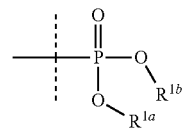

and $R^{1a}$ and $R^{1b}$ are each independently H, $(C_1-C_4)$alkyl, or —$CH_2OCO_2(C_1-C_4)$alkyl.

In another embodiment, X is

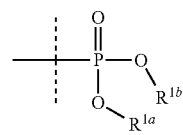

and $R^{1a}$ and $R^{1b}$ are each independently H or methyl.

In another embodiment, X is

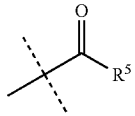

and $R^5$ is $(C_1-C_6)$alkyl substituted by —OH, —OP(=O)(OH)$_2$, —NH$_2$, or —NHCO$(C_1-C_4)$alkyl, wherein the $(C_1-C_4)$alkyl group of said —NHCO$(C_1-C_4)$alkyl is optionally substituted by —NH$_2$.

In another embodiment, X is

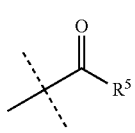

and $R^5$ is $(C_1-C_6)$alkyl substituted by —OH or —NH$_2$.

In another embodiment, X is

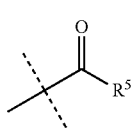

and $R^5$ is $(C_1-C_6)$alkyl substituted by —NH$_2$.

In another embodiment, X is

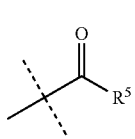

and $R^5$ is —CH(NH$_2$)$(C_1-C_4)$alkyl.

In a preferred embodiment, X is

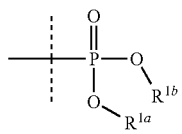

and $R^{1a}$ and $R^{1b}$ are each independently H, or a pharmaceutically acceptable salt thereof.

In another preferred embodiment, X is

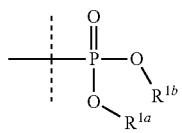

and $R^{1a}$ and $R^{1b}$ are each independently H, or a pharmaceutically acceptable salt thereof, or a hydrate thereof In another preferred embodiment, X is

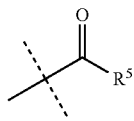

and $R^5$ is $(C_1-C_4)$alkyl substituted by —NH$_2$.

Representative compounds of this invention include:
2-((4-(benzo[d]thiazol-5-ylamino)-6-(tert-butylsulfonyl)quinazolin-7-yl)oxy)ethyl dihydrogen phosphate,
(S)-2-((4-(benzo[d]thiazol-5-ylamino)-6-(tert-butylsulfonyl)quinazolin-7-yl)oxy)ethyl 2-amino-3-methylbutanoate,
(R)-2-((4-(benzo[d]thiazol-5-ylamino)-6-(tert-butylsulfonyl)quinazolin-7-yl)oxy)ethyl 2-amino-3-methylbutanoate, and
(2S,3S)-2-((4-(benzo[d]thiazol-5-ylamino)-6-(tert-butylsulfonyl)quinazolin-7-yl)oxy)ethyl 2-amino-3-methylpentanoate,
or a salt thereof In another embodiment, representative compounds of this invention include the compounds of Examples 1-7, specifically:
2-((4-(benzo[d]thiazol-5-ylamino)-6-(tert-butylsulfonyl)quinazolin-7-yl)oxy)ethyl dihydrogen phosphate,
2-((4-(benzo[d]thiazol-5-ylamino)-6-(tert-butylsulfonyl)quinazolin-7-yl)oxy)ethyl disodium phosphate,
calcium (I) 2-((4-(benzo[d]thiazol-5-ylamino)-6-(tert-butylsulfonyl)quinazolin-7-yl)oxy)ethyl hydrogen phosphate trihydrate,
2-((4-(benzo[d]thiazol-5-ylamino)-6-(tert-butylsulfonyl)quinazolin-7-yl)oxy)ethyl dihydrogen phosphate hydrochloride monohydrate,
(S)-2-((4-(benzo[d]thiazol-5-ylamino)-6-(tert-butylsulfonyl)quinazolin-7-yl)oxy)ethyl 2-amino-3-methylbutanoate, dihydrochloride,
(R)-2-((4-(benzo[d]thiazol-5-ylamino)-6-(tert-butylsulfonyl)quinazolin-7-yl)oxy)ethyl 2-amino-3-methylbutanoate, dihydrochloride, and
(2S,3S)-2-((4-(benzo[d]thiazol-5-ylamino)-6-(tert-butylsulfonyl)quinazolin-7-yl)oxy)ethyl 2-amino-3-methylpentanoate.

In another embodiment representative compounds of this invention include:
2-((4-(benzo[d]thiazol-5-ylamino)-6-(tert-butylsulfonyl)quinazolin-7-yl)oxy)ethyl dihydrogen phosphate,
2-((4-(benzo[d]thiazol-5-ylamino)-6-(tert-butylsulfonyl)quinazolin-7-yl)oxy)ethyl disodium phosphate, and
(S)-2-((4-(benzo[d]thiazol-5-ylamino)-6-(tert-butylsulfonyl)quinazolin-7-yl)oxy)ethyl 2-amino-3-methylbutanoate, dihydrochloride.

It will be appreciated that the present invention covers compounds of Formula (I) as the free base or free acid and as salts thereof, for example as a pharmaceutically acceptable salt thereof. In one embodiment the invention relates to compounds of Formula (I) in the form of a free base or free acid. In another embodiment the invention relates to compounds of Formula (I) or a pharmaceutically acceptable salt thereof. It will further be appreciated that compounds of Formula (I) and salts thereof may exist in hydrated from, such as the monohydrate or the trihydrate.

In one embodiment, the compound of the invention is 2-((4-(benzo[d]thiazol-5-ylamino)-6-(tert-butylsulfonyl)quinazolin-7-yl)oxy)ethyl dihydrogen phosphate as the free acid. In another embodiment, the compound of the invention is 2-((4-(benzo[d]thiazol-5-ylamino)-6-(tert-butylsulfonyl)quinazolin-7-yl)oxy)ethyl dihydrogen phosphate or a salt thereof. In another embodiment, the compound of the invention is 2-((4-(benzo[d]thiazol-5-ylamino)-6-(tert-butylsulfonyl)quinazolin-7-yl)oxy)ethyl dihydrogen phosphate or a pharmaceutically acceptable salt thereof. In another embodiment, the compound of the invention is 2-((4-(benzo[d]thiazol-5-ylamino)-6-(tert-butylsulfonyl)quinazolin-7-yl)oxy)ethyl dihydrogen phosphate or a hydrate thereof. In another embodiment, the compound of the invention is a pharmaceutically acceptable salt of 2-((4-(benzo[d]thiazol-5-ylamino)-6-(tert-butylsulfonyl)quinazolin-7-yl)oxy)ethyl dihydrogen phosphate or a hydrate thereof. In yet another embodiment, the compound of the invention is a sodium, calcium or hydrochloride salt of 2-((4-(benzo[d]thiazol-5-ylamino)-6-(tert-butylsulfonyl)quinazolin-7-yl)oxy)ethyl dihydrogen phosphate, or a hydrate thereof.

In a specific embodiment, the compound of the invention is 2-((4-(benzo[d]thiazol-5-ylamino)-6-(tert-butylsulfonyl)quinazolin-7-yl)oxy)ethyl disodium phosphate.

In another specific embodiment, the compound of the invention is calcium (I) 2-((4-(benzo[d]thiazol-5-ylamino)-6-(tert-butylsulfonyl)quinazolin-7-yl)oxy)ethyl hydrogen phosphate trihydrate. In a further specific embodiment, the compound of the invention is calcium (I) 2-((4-(benzo[d]thiazol-5-ylamino)-6-(tert-butylsulfonyl)quinazolin-7-yl)oxy)ethyl hydrogen phosphate trihydrate having the PXRD of FIG. 1.

Figure 2:
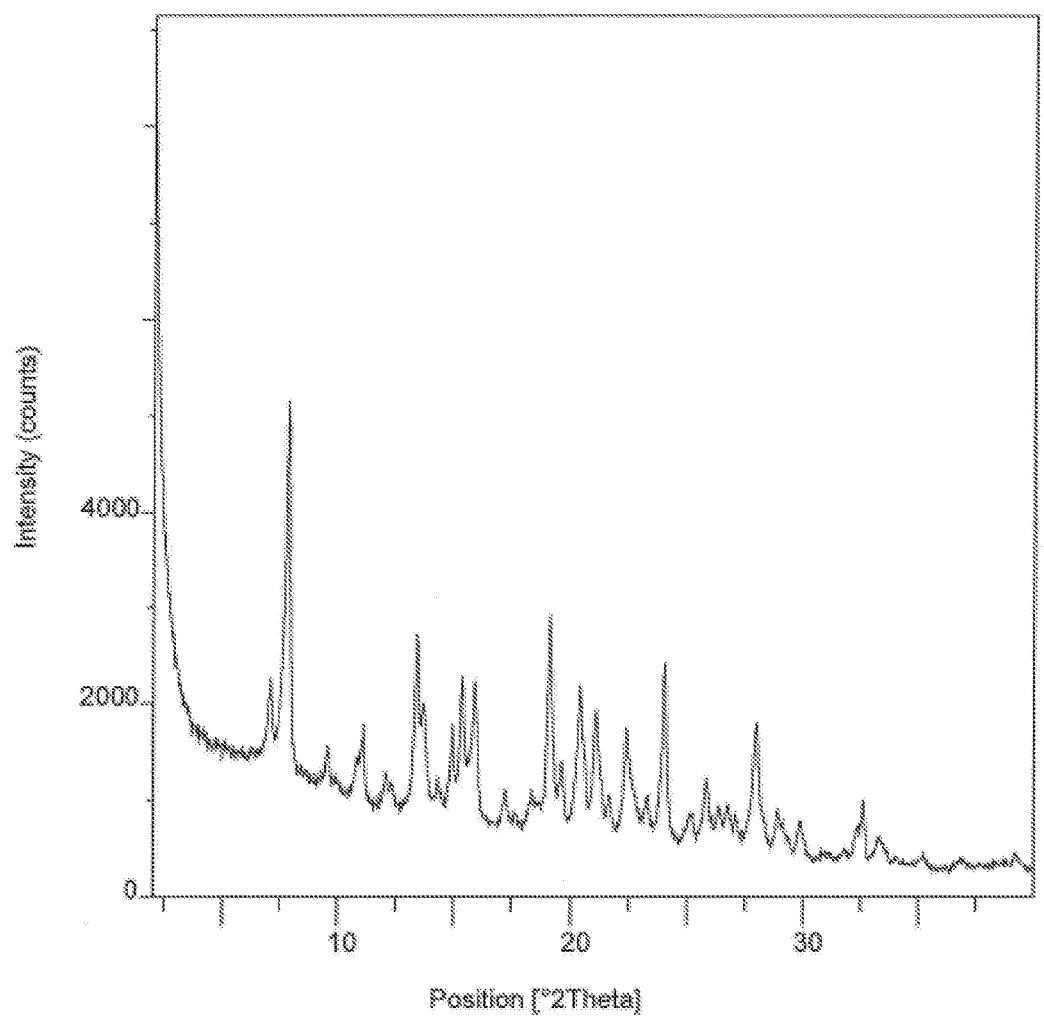
FIG. 2 is a PXRD pattern of a crystalline form of 2-((4-(benzo[d]thiazol-5-ylamino)-6-(tert-butylsulfonyl) quinazolin-7-yl)oxy)ethyl dihydrogen phosphate hydrochloride monohydrate.

In yet another specific embodiment, the compound of the invention is 2-((4-(benzo[d]thiazol-5-ylamino)-6-(tert-butylsulfonyl)quinazolin-7-yl)oxy)ethyl dihydrogen phosphate hydrochloride monohydrate. In yet a further specific embodiment, the compound of the invention is 2-((4-(benzo[d]thiazol-5-ylamino)-6-(tert-butyl sulfonyl)quinazolin-7-yl)oxy)ethyl dihydrogen phosphate hydrochloride monohydrate having the PXRD of FIG. 2.

In another embodiment the compound of the invention is (S)-2-((4-(benzo[d]thiazol-5-ylamino)-6-(tert-butylsulfonyl)quinazolin-7-yl)oxy)ethyl 2-amino-3-methylbutanoate as the free base. In another embodiment the compound of the invention is (S)-2-((4-(benzo[d]thiazol-5-ylamino)-6-(tert-butylsulfonyl)quinazolin-7-yl)oxy)ethyl 2-amino-3-methylbutanoate or a salt thereof. In another embodiment the compound of the invention is (S)-2-((4-(benzo[d]thiazol-5- ylamino)-6-(tert-butylsulfonyl)quinazolin-7-yl)oxy)ethyl 2-amino-3-methylbutanoate or a pharmaceutically acceptable salt thereof.

In another embodiment the compound of the invention is (R)-2-((4-(benzo[d]thiazol-5-ylamino)-6-(tert-butylsulfonyl)quinazolin-7-yl)oxy)ethyl 2-amino-3-methylbutanoate as the free base. In another embodiment the compound of the invention is (R)-2-((4-(benzo[d]thiazol-5-ylamino)-6-(tert-butylsulfonyl)quinazolin-7-yl)oxy)ethyl 2-amino-3-methylbutanoate or a salt thereof. In another embodiment the compound of the invention is (R)-2-((4-(benzo[d]thiazol-5-ylamino)-6-(tert-butylsulfonyl)quinazolin-7-yl)oxy)ethyl 2-amino-3-methylbutanoate or a pharmaceutically acceptable salt thereof.

In a further embodiment the compound of the invention is (2S,3S)-2-((4-(benzo[d]thiazol-5-ylamino)-6-(tert-butylsulfonyl)quinazolin-7-yl)oxy)ethyl 2-amino-3-methylpentanoate as the free base. In a further embodiment the compound of the invention is (2S,3S)-2-((4-(benzo[d]thiazol-5-ylamino)-6-(tert-butylsulfonyl)quinazolin-7-yl)oxy)ethyl 2-amino-3-methylpentanoate or a salt thereof. In a further embodiment the compound of the invention is (2S,3S)-2-((4-(benzo[d]thiazol-5-ylamino)-6-(tert-butylsulfonyl)quinazolin-7-yl)oxy)ethyl 2-amino-3-methylpentanoate or a pharmaceutically acceptable salt thereof.

Accordingly, a compound of the invention includes a compound of Formula (I), particularly the specific compounds described herein, or a salt thereof, particularly a pharmaceutically acceptable salt thereof. Specifically, a compound of the invention includes a compound of Formula (I), or a pharmaceutically acceptable salt thereof, or a hydrate thereof, or a hydrate of a pharmaceutically acceptable salt of a compound of Formula (I) and particularly the specific compounds described herein. In one embodiment, the invention is directed to a method of inhibiting RIP2 kinase comprising administering to a host a compound of the invention. In another embodiment, the invention is directed to a method of treating a RIP2 kinase-mediated disease or disorder comprising administering a therapeutically effective amount of a compound of the invention to a human in need thereof.

This invention is directed to a method of treating a disease or disorder mediated by inhibition of RIP2 kinase comprising administering a therapeutically effective amount of a compound of the invention to a human in need thereof. This invention is particularly directed to a method of treating a disease or disorder mediated by inhibition of RIP2 kinase comprising administering a therapeutically effective amount of the compound according to Formula (I) or pharmaceutically acceptable salt thereof to a human in need thereof.

The invention is still further directed to the use of a compound of the invention or a pharmaceutical composition comprising a compound of the invention to inhibit RIP2 kinase and/or treat a RIP2 kinase-mediated disease or disorder.

The compounds according to Formula (I) may contain one or more asymmetric center (also referred to as a chiral center) and may, therefore, exist as individual enantiomers, diastereomers, or other stereoisomeric forms, or as mixtures thereof. Where the stereochemistry of a chiral center present in a compound of this invention (e.g., compound name) or in any chemical structure illustrated herein is not specified, the compound, compound name, or structure is intended to encompass all individual stereoisomers and all mixtures thereof. Thus, compounds according to Formula (I) containing one or more chiral center may be present as racemic mixtures, enantiomerically enriched mixtures, or as enantiomerically pure individual stereoisomers.

Individual stereoisomers of a compound according to Formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

It is to be understood that a solid form of a compound of the invention may exist in crystalline forms, non-crystalline forms or a mixture thereof. Such crystalline forms may also exhibit polymorphism (i.e. the capacity to occur in different crystalline forms). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

When a compound of the invention is a base (contains a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, and the like, or with a pyranosidyl acid, such as glucuronic acid or galacturonic acid, or with an alpha-hydroxy acid, such as citric acid or tartaric acid, or with an amino acid, such as aspartic acid or glutamic acid, or with an aromatic acid, such as benzoic acid or cinnamic acid, or with a sulfonic acid, such as p-toluenesulfonic acid, methanesulfonic acid, ethanesulfonic acid or the like.

Suitable addition salts include acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, edetate, edisylate, estolate, esylate, ethanedisulfonate, ethanesulfonate, formate, fumarate, gluceptate, gluconate, glutamate, glycollate, glycollylarsanilate, hexylresorcinate, hydrabamine, hydrobromide, hydrochloride, dihydrochloride, hydrofumarate, hydrogen phosphate, hydroiodide, hydromaleate, hydrosuccinate, hydroxynaphthoate, isethionate, itaconate, lactate, lactobionate, laurate, malate, maleate, mandelate, mesylate, methylsulfate, monopotassium maleate, mucate, napsylate, nitrate, N-methylglucamine, oxalate, oxaloacetate, pamoate (embonate), palmate, palmitate, pantothenate, phosphate/diphosphate, pyruvate, polygalacturonate, propionate, saccharate, salicylate, stearate, subacetate, succinate, sulfate, tannate, tartrate, teoclate, tosylate, triethiodide, trifluoroacetate and valerate.

Other exemplary acid addition salts include pyrosulfate, sulfite, bisulfate, decanoate, caprylate, acrylate, isobutyrate, caproate, heptanoate, propiolate, oxalate, malonate, suberate, sebacate, butyne-1,4-dioate, hexyne-1,6-dioate, chlorobenzoate, methylbenzoate, dinitrobenzoate, hydroxybenzoate, methoxybenzoate, phthalate, phenylacetate, phenylpropionate, phenylbutrate, lactate, γ-hydroxybutyrate, mandelate, and sulfonates, such as xylenesulfonate, propanesulfonate, naphthalene-1-sulfonate and naphthalene-2-sulfonate.

If an inventive basic compound is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

When a compound of the invention is an acid (contains an acidic moiety), a desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary, and tertiary amines, and cyclic amines, such as N-methyl-D-glucamine, diethylamine, isopropylamine, trimethylamine, ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Because of their potential use in medicine, the salts of the compounds of Formula (I) are preferably pharmaceutically acceptable salts. Suitable pharmaceutically acceptable salts include acid or base addition salts, such as those described by Berge, Bighley and Monkhouse J. Pharm. Sci (1977) 66, pp 1-19 and "Pharmaceutical Salts: Properties, Selection, and Use, 2nd Revised Edition," P. H. Stahl and C. G. Wermuth (eds.), Wiley, Hoboken, N.J., US (2011). The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable salt(s)" refers to a compound which is suitable for pharmaceutical use. Salt and solvate (e.g. hydrates and hydrates of salts) forms of the compounds of Formula (I) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their salts and solvates.

Examples of pharmaceutically acceptable acid-addition salts include acetate, adipate, ascorbate, aspartate, benzenesulfonate, benzoate, camphorate, camphor-sulfonate (camsylate), caprate (decanoate), caproate (hexanoate), caprylate (octanoate), carbonate, bicarbonate, cinnamate, citrate, cyclamate, dodecylsulfate (estolate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hippurate, hydrobromide, hydrochloride, hydroiodide, isobutyrate, lactate, lactobionate, laurate, maleate, malate, malonate, mandelate, methanesulfonate (mesylate), naphthalene-1,5-disulfonate (napadisylate), naphthalene-sulfonate (napsylate), nicotinate, nitrate, oleate, oxalate, palmitate, pamoate, phosphate, diphosphate, proprionate, pyroglutamate, salicylate, sebacate, stearate, succinate, sulfate, tartrate, thiocyanate, tosylate, undecylenate, 1-hydroxy-2-naphthoate, 2,2-dichloroacetate, 2-hydroxyethanesulfonate (isethionate), 2-oxoglutarate, 4-acetamidobenzoate, and 4-aminosalicylate. In one embodiment the pharmaceutically acceptable acid addition salt is hydrochloride (e.g., a monohydrochloride or dihydrochloride salt). Non-pharmaceutically acceptable salts, e.g. trifluoroacetate, may be used, for example in the isolation of a compound of Formula (I), and are included within the scope of this invention.

Examples of pharmaceutically acceptable base-addition salts include ammonium, lithium, sodium, potassium, calcium, magnesium, aluminum salts, zinc salts, trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, glucamine, N-methylglucamine, collidine, quinine, quinoline, lysine and arginine. In one embodiment the pharmaceutically acceptable base-addition salt is sodium or calcium. In another embodiment the pharmaceutically acceptable base-addition salt is sodium. In another embodiment the pharmaceutically acceptable base-addition salt is calcium.

Certain of the compounds of the invention may form salts with one or more equivalents of an acid (if the compound contains a basic moiety) or a base (if the compound contains an acidic moiety). The present invention includes within its scope all possible stoichiometric and non-stoichiometric salt forms.

Compounds of the invention having both a basic and acidic moiety may be in the form of zwitterions, acid-addition salt of the basic moiety or base salts of the acidic moiety.

This invention also provides for the conversion of one pharmaceutically acceptable salt of a compound of this invention into another pharmaceutically acceptable salt of a compound of this invention.

If an inventive basic compound is isolated as a salt, the corresponding free acid or free base form of that compound may be prepared by any suitable method known to the art.

For solvates of the compounds of Formula (I), including solvates of salts of the compounds of Formula (I), that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates, particularly hydrates, for example the monohydrate or trihydrate. Accordingly, a compound of this invention includes a compound of Formula (I), or a salt thereof, particularly a pharmaceutically acceptable salt thereof, or a hydrate thereof, a hydrate of a pharmaceutically acceptable salt of a compound of Formula (I) and particularly includes each compound described in the Examples. Thus the invention provides a compound of Formula (I) or a salt thereof, especially a pharmaceutically acceptable salt thereof, as a solvate, particularly as a hydrate, such as a monohydrate or trihydrate.

Because the compounds of Formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

The compounds of the invention may be particularly useful for treatment of RIP2 kinase-mediated diseases or disorders, particularly diseases or disorders mediated by inhibition of RIP2 kinase, such as uveitis, interleukin-1 converting enzyme (ICE, also known as Caspase-1) associated fever syndrome (ICE fever), dermatitis, acute lung injury, type 2 diabetes mellitus, arthritis (specifically rheumatoid arthritis), inflammatory bowel disorders (such as ulcerative colitis and Crohn's disease), early-onset inflammatory bowel disease, extraintestinal inflammatory bowel disease, prevention of ischemia reperfusion injury in solid organs (specifically kidney) in response ischemia induced by cardiac surgery, organ transplant, sepsis and other insults, liver diseases (non-alcohol steatohepatitis, alcohol steatohepatitis, and autoimmune hepatitis), allergic diseases (such as asthma), transplant reactions (such as graft versus host disease), autoimmune diseases (such as systemic lupus erythematosus, and multiple sclerosis), and granulomateous disorders (such as sarcoidosis, Blau syndrome, early-onset sarcoidosis, Wegner's granulomatosis, and interstitial pulmonary disease).

The compounds of this invention may be particularly useful in the treatment of uveitis, ICE fever, Blau Syndrome, early-onset sarcoidosis, ulcerative colitis, Crohn's disease, Wegener's granulamatosis and sarcoidosis.

In one embodiment the invention is directed to a method of treating uveitis comprising administering a therapeutically effective amount of the compound according to Formula (I) or a pharmaceutically acceptable salt thereof, to a human in need thereof. In another embodiment the invention is directed to a method of treating interleukin-1 converting enzyme associated fever syndrome comprising administering a therapeutically effective amount of the compound according to Formula (I) or a pharmaceutically acceptable salt thereof, to a human in need thereof. In another embodiment the invention is directed to a method of treating Blau syndrome comprising administering a therapeutically effective amount of the compound according to Formula (I) or a pharmaceutically acceptable salt thereof, to a human in need thereof. In another embodiment the invention is directed to a method of treating early-onset sarcoidosis comprising administering a therapeutically effective amount of the compound according to Formula (I) or a pharmaceutically acceptable salt thereof, to a human in need thereof. In another embodiment the invention is directed to a method of treating ulcerative colitis comprising administering a therapeutically effective amount of the compound according to Formula (I) or a pharmaceutically acceptable salt thereof, to a human in need thereof. In another embodiment the invention is directed to a method of treating Crohn's disease comprising administering a therapeutically effective amount of the compound according to Formula (I) or a pharmaceutically acceptable salt thereof, to a human in need thereof. In another embodiment the invention is directed to a method of treating Wegner's Granulomatosis comprising administering a therapeutically effective amount of the compound according to Formula (I) or a pharmaceutically acceptable salt thereof, to a human in need thereof. In a further embodiment the invention is directed to a method of treating sarcoidosis comprising administering a therapeutically effective amount of the compound according to Formula (I) or a pharmaceutically acceptable salt thereof, to a human in need thereof.

Treatment of RIP2 kinase-mediated diseases or disorders, or more broadly, treatment of immune mediated diseases including, but not limited to, allergic diseases, autoimmune diseases, prevention of transplant rejection and the like, may be achieved using a compound of this invention as a monotherapy, or in dual or multiple combination therapy, particularly for the treatment of refractory cases, such as in combination with other anti-inflammatory and/or anti-TNF agents, which may be administered in therapeutically effective amounts as is known in the art.

The compounds of Formula (I) and pharmaceutically acceptable salts thereof may be employed alone or in combination with other therapeutic agents. Combination therapies according to the present invention thus comprise the administration of at least one compound of Formula (I) or a pharmaceutically acceptable salt thereof, and the use of at least one other therapeutically active agent. Preferably, combination therapies according to the present invention comprise the administration of at least one compound of Formula (I) or a pharmaceutically acceptable salt thereof, and at least one other therapeutically active agent. The compound(s) of Formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of Formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of Formula (I) or a pharmaceutically acceptable salt thereof, together with one or more other therapeutically active agents.

Thus in one aspect, the compound of Formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example an anti-inflammatory agent and/or an anti-TNF agent.

The compounds of this invention may be administered in combination with corticosteroids and/or anti-TNF agents to treat Blau syndrome, early-onset sarcoidosis; or in combination with anti-TNF biologics or other anti-inflammatory biologics to treat Crohn's Disease; or in combination with 5-ASA (mesalamine) or sulfasalazine to treat ulcerative colitis; or in combination with low-dose corticosteroids and/or methotrexate to treat Wegener's granulamatosis or sarcoidosis or interstitial pulmonary disease; or in combination with a biologic (e.g. anti-TNF, anti-IL-6, etc.) to treat rheumatoid arthritis; or in combination with anti-IL6 and/or methotrexate to treat ICE fever.

Examples of suitable anti-inflammatory agents include 5-aminosalicyclic acid and mesalamine preparations, sulfasalazine, hydroxycloroquine, thiopurines (azathioprin, mercaptopurin), methotrexate, cyclophosphamide, cyclosporine, JAK inhibitors (tofacitinib), corticosteroids, particularly low-dose corticosteroids (such as prednisone (Deltasone®) and bundesonide) and anti-inflammatory biologics such as anti-IL6R mAbs (Actemra® (tocilizumab)), anti-IL6 biologics, anti-IL1 or IL12 or IL23 biologics (ustekinumab (Stelara®)), anti-integrin agents (natalizumab (Tysabri®)), anti-CD20 mAbs (rituximab (Rituxan®) and ofatumumab (Arzerra®)), and other agents, such as abatacept (Orencia®), anakinra (Kineret®), and belimumab (Benlysta®), CD4 biologics and other cytokine inhibitors or biologics to T-cell or B-cell receptors or interleukins. Examples of suitable anti-TNF agents include the anti-TNF biologics such as Enbrel® (etanecerpt), Humira® (adalimumab), Remicade® (infliximab), Cimzia® (certolizumab), and Simponi® (golimumab).

This invention provides a compound of the invention for use in therapy. This invention also provides a compound of Formula (I), or a pharmaceutically acceptable salt thereof, for use in therapy. Specifically, this invention provides the compounds described herein for use in therapy.

In another embodiment, this invention provides a compound of the invention for use in the treatment of a disease or disorder mediated by inhibition of RIP2 kinase. In another embodiment, this invention provides a compound of Formula (I), or a pharmaceutically acceptable salt thereof, for use in the treatment of a disease or disorder mediated by inhibition of RIP2 kinase. Specifically, this invention provides the compounds described herein for use in the treatment of a disease or disorder mediated by inhibition of RIP2 kinase. In another embodiment this invention provides a compound of Formula (I), or a pharmaceutically acceptable salt thereof, for use in the treatment of uveitis, interleukin-1 converting enzyme associated fever syndrome, dermatitis, acute lung injury, type 2 diabetes mellitus, arthritis, rheumatoid arthritis, ulcerative colitis, Crohn's disease, early-onset inflammatory bowel disease, extraintestinal inflammatory bowel disease, prevention of ischemia reperfusion injury in solid organ transplant, non-alcohol steatohepatitis, alcohol steatohepatitis, autoimmune hepatitis, asthma, graft versus host disease, systemic lupus erythematosus, multiple sclerosis, sarcoidosis, Blau syndrome/early-onset sarcoidosis, Wegner's granulomatosis or interstitial pulmonary disease. In another embodiment this invention provides a compound of Formula (I), or a pharmaceutically acceptable salt thereof, for use in the treatment of uveitis. In another embodiment this invention provides a compound of Formula (I), or a pharmaceutically acceptable salt thereof, for use in the treatment of interleukin-1 converting enzyme associated fever syndrome. In another embodiment this invention provides a compound of Formula (I), or a pharmaceutically acceptable salt thereof, for use in the treatment of Blau syndrome. In another embodiment this invention provides a compound of Formula (I), or a pharmaceutically acceptable salt thereof, for use in the treatment of early-onset sarcoidosis. In another embodiment this invention provides a compound of Formula (I), or a pharmaceutically acceptable salt thereof, for use in the treatment of ulcerative colitis. In another embodiment this invention provides a compound of Formula (I), or a pharmaceutically acceptable salt thereof, for use in the treatment of Crohn's disease. In another embodiment this invention provides a compound of Formula (I), or a pharmaceutically acceptable salt thereof, for use in the treatment of early-onset inflammatory bowel disease. In another embodiment this invention provides a compound of Formula (I), or a pharmaceutically acceptable salt thereof, for use in the treatment of extraintestinal inflammatory bowel disease. In another embodiment this invention provides a compound of Formula (I), or a pharmaceutically acceptable salt thereof, for use in the treatment of Wegner's Granulomatosis. In another embodiment this invention provides a compound of Formula (I), or a pharmaceutically acceptable salt thereof, for use in the treatment of sarcoidosis.

This invention specifically provides for the use of a compound of Formula (I), or a pharmaceutically acceptable salt thereof, as an active therapeutic substance in the treatment of a RIP2 kinase-mediated disease or disorder, for example the diseases and disorders recited herein. More specifically, this invention provides for the use of a compound of Formula (I), or a pharmaceutically acceptable salt thereof, for the treatment of a disease or disorder mediated by inhibition of RIP2 kinase. This invention specifically provides for the use of the compounds described herein for the treatment of a disease or disorder mediated by inhibition of RIP2 kinase. Accordingly, the invention provides for the use of a compound of Formula (I), or a pharmaceutically acceptable salt thereof, as an active therapeutic substance in the treatment of a human in need thereof with a disease mediated by inhibition of RIP2 kinase.

The invention also provides for the use of a compound of Formula (I), or a pharmaceutically acceptable salt thereof, in the manufacture of a medicament for use in the treatment of a RIP2 kinase-mediated disease or disorder, for example the diseases and disorders recited herein. More specifically, this invention provides for the use of a compound of Formula (I), or a pharmaceutically acceptable salt thereof, in the manufacture of a medicament for the treatment of a disease or disorder mediated by inhibition of RIP2 kinase. Accordingly, the invention provides for the use of a compound of Formula (I), or a pharmaceutically acceptable salt thereof, in the manufacture of a medicament for use in the treatment of a human in need thereof with a disease or disorder mediated by inhibition of RIP2 kinase. In one embodiment this invention provides for the use of a compound of Formula (I), or a pharmaceutically acceptable salt thereof, in the manufacture of a medicament for use in the treatment of uveitis, interleukin-1 converting enzyme associated fever syndrome, dermatitis, acute lung injury, type 2 diabetes mellitus, arthritis, rheumatoid arthritis, ulcerative colitis, Crohn's disease, early-onset inflammatory bowel disease, extraintestinal inflammatory bowel disease, prevention of ischemia reperfusion injury in solid organ transplant, non-alcohol steatohepatitis, alcohol steatohepatitis, autoimmune hepatitis, asthma, graft versus host disease, systemic lupus erythematosus, multiple sclerosis, sarcoidosis, Blau syndrome/early-onset sarcoidosis, Wegner's granulomatosis or interstitial pulmonary disease. In another embodiment this invention provides for the use of a compound of Formula (I), or a pharmaceutically acceptable salt thereof, in the manufacture of a medicament for use in the treatment of uveitis. In another embodiment this invention provides for the use of a compound of Formula (I), or a pharmaceutically acceptable salt thereof, in the manufacture of a medicament for use in the treatment of interleukin-1 converting enzyme associated fever syndrome. In another embodiment this invention provides for the use of a compound of Formula (I), or a pharmaceutically acceptable salt thereof, in the manufacture of a medicament for use in the treatment of early-onset sarcoidosis. In another embodiment this invention provides for the use of a compound of Formula (I), or a pharmaceutically acceptable salt thereof, in the manufacture of a medicament for use in the treatment of ulcerative colitis. In another embodiment this invention provides for the use of a compound of Formula (I), or a pharmaceutically acceptable salt thereof, in the manufacture of a medicament for use in the treatment of Crohn's disease. In another embodiment this invention provides for the use of a compound of Formula (I), or a pharmaceutically acceptable salt thereof, in the manufacture of a medicament for use in the treatment of Wegner's Granulomatosis. In another embodiment this invention provides for the use of a compound of Formula (I), or a pharmaceutically acceptable salt thereof, in the manufacture of a medicament for use in the treatment of sarcoidosis. In another embodiment this invention provides for the use of a compound of Formula (I), or a pharmaceutically acceptable salt thereof, in the manufacture of a medicament for use in the treatment of early-onset inflammatory bowel disease. In another embodiment this invention provides for the use of a compound of Formula (I), or a pharmaceutically acceptable salt thereof, in the manufacture of a medicament for use in the treatment of extraintestinal inflammatory bowel disease. In a further embodiment this invention provides for the use of a compound of Formula (I), or a pharmaceutically acceptable salt thereof, in the manufacture of a medicament for use in the treatment of Blau syndrome.

A therapeutically "effective amount" is intended to mean that amount of a compound that, when administered to a patient in need of such treatment, is sufficient to effect treatment, as defined herein. Thus, e.g., a therapeutically effective amount of a compound of Formula (I), or a pharmaceutically acceptable salt thereof, or hydrate thereof, is a quantity of an inventive agent that, when administered to a human in need thereof, is sufficient to modulate or inhibit the activity of RIP2 kinase such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmaceutical characteristics), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this invention in any conventionally acceptable manner, for example for prevention, retardation, prophylaxis, therapy or cure of a mediated disease or disorder. Specific diseases and disorders that may be particularly susceptible to treatment using a compound of this invention are described herein.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

For use in therapy, the compounds of the invention will be normally, but not necessarily, formulated into a pharmaceutical composition prior to administration to a patient. Accordingly, the invention also is directed to pharmaceutical compositions comprising a compound of the invention and one or more pharmaceutically acceptable excipients.

In one embodiment there is provided a pharmaceutical composition comprising 2-((4-(benzo[d]thiazol-5-ylamino)-6-(tert-butylsulfonyl)quinazolin-7-yl)oxy)ethyl dihydrogen phosphate as the free acid and one or more pharmaceutically acceptable excipients. In another embodiment, there is provided a pharmaceutical composition comprising 2-((4-(benzo[d]thiazol-5-ylamino)-6-(tert-butylsulfonyl)quinazolin-7-yl)oxy)ethyl dihydrogen phosphate or a pharmaceutically acceptable salt thereof and one or more pharmaceutically acceptable excipients. In another embodiment, there is provided a pharmaceutical composition comprising 2-((4-(benzo[d]thiazol-5-ylamino)-6-(tert-butylsulfonyl)quinazolin-7-yl)oxy)ethyl dihydrogen phosphate or a hydrate thereof and one or more pharmaceutically acceptable excipients. In another embodiment, there is provided a pharmaceutical composition comprising a pharmaceutically acceptable salt of 2-((4-(benzo[d]thiazol-5-ylamino)-6-(tert-butylsulfonyl)quinazolin-7-yl)oxy)ethyl dihydrogen phosphate or a hydrate thereof and one or more pharmaceutically acceptable excipients. In yet another embodiment, there is provided a pharmaceutical composition comprising a sodium, calcium or hydrochloride salt of 2-((4-(benzo[d]thiazol-5-ylamino)-6-(tert-butylsulfonyl)quinazolin-7-yl)oxy)ethyl dihydrogen phosphate, or a hydrate thereof and one or more pharmaceutically acceptable excipients.

In a specific embodiment, there is provided a pharmaceutical composition comprising 2-((4-(benzo[d]thiazol-5-ylamino)-6-(tert-butylsulfonyl)quinazolin-7-yl)oxy)ethyl disodium phosphate and one or more pharmaceutically acceptable excipients.

In another specific embodiment, there is provided a pharmaceutical composition comprising calcium (I) 2-((4-(benzo[d]thiazol-5-ylamino)-6-(tert-butylsulfonyl)quinazolin-7-yl)oxy)ethyl hydrogen phosphate trihydrate and one or more pharmaceutically acceptable excipients. In a further specific embodiment, there is provided a pharmaceutical composition comprising calcium (I) 2-((4-(benzo[d]thiazol-5-ylamino)-6-(tert-butylsulfonyl)quinazolin-7-yl)oxy)ethyl hydrogen phosphate trihydrate having the PXRD of FIG. 1 and one or more pharmaceutically acceptable excipients.

In yet another specific embodiment, there is provided a pharmaceutical composition comprising 2-((4-(benzo[d]thiazol-5-ylamino)-6-(tert-butylsulfonyl)quinazolin-7-yl)oxy)ethyl dihydrogen phosphate hydrochloride monohydrate and one or more pharmaceutically acceptable excipients. In yet a further specific embodiment, there is provided a pharmaceutical composition comprising 2-((4-(benzo[d]thiazol-5-ylamino)-6-(tert-butylsulfonyl)quinazolin-7-yl)oxy)ethyl dihydrogen phosphate hydrochloride monohydrate having the PXRD of FIG. 2 and one or more pharmaceutically acceptable excipients.

In another embodiment there is provided a pharmaceutical composition comprising (S)-2-((4-(benzo[d]thiazol-5-ylamino)-6-(tert-butylsulfonyl)quinazolin-7-yl)oxy)ethyl 2-amino-3-methylbutanoate as the free base and one or more pharmaceutically acceptable excipients. In another embodiment there is provided a pharmaceutical composition comprising (S)-2-((4-(benzo[d]thiazol-5-ylamino)-6-(tert-butylsulfonyl)quinazolin-7-yl)oxy)ethyl 2-amino-3-methylbutanoate or a pharmaceutically acceptable salt thereof and one or more pharmaceutically acceptable excipients.

In another embodiment there is provided a pharmaceutical composition comprising (R)-2-((4-(benzo[d]thiazol-5-ylamino)-6-(tert-butylsulfonyl)quinazolin-7-yl)oxy)ethyl 2-amino-3-methylbutanoate as the free base and one or more pharmaceutically acceptable excipients. In another embodiment there is provided a pharmaceutical composition comprising (R)-2-((4-(benzo[d]thiazol-5-ylamino)-6-(tert-butylsulfonyl)quinazolin-7-yl)oxy)ethyl 2-amino-3-methylbutanoate or a pharmaceutically acceptable salt thereof and one or more pharmaceutically acceptable excipients.

In a further embodiment there is provided a pharmaceutical composition comprising (2S,3S)-2-((4-(benzo[d]thiazol-5-ylamino)-6-(tert-butylsulfonyl)quinazolin-7-yl)oxy)ethyl 2-amino-3-methylpentanoate as the free base and one or more pharmaceutically acceptable excipients. In a further embodiment there is provided a pharmaceutical composition comprising (2S,3S)-2-((4-(benzo[d]thiazol-5-ylamino)-6-(tert-butylsulfonyl)quinazolin-7-yl)oxy)ethyl 2-amino-3-methylpentanoate or a pharmaceutically acceptable salt thereof and one or more pharmaceutically acceptable excipients.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula (I), or a salt, particularly a pharmaceutically acceptable salt, thereof). When prepared in unit dosage form, the pharmaceutical compositions may contain from 1 mg to 1000 mg of a compound of this invention.

As provided herein, unit dosage forms (pharmaceutical compositions) containing from 1 mg to 1000 mg of a compound of the invention may be administered one, two, three, or four times per day, preferably one, two, or three times per day, and more preferably, one or two times per day, to effect treatment of a RIP2 mediated disease or disorder. The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional pharmaceutically active compounds.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Names for the intermediate and final compounds described herein were generated using the software naming program ACD/Name Pro V6.02 available from Advanced Chemistry Development, Inc., 110 Yonge Street, 14$^{th}$ Floor, Toronto, Ontario, Canada, M5C 1T4 (http://www.acdlabs.com/) or the naming program in ChemDraw, Struct=Name Pro 12.0, as part of ChemBioDraw Ultra, available from CambridgeSoft. 100 CambridgePark Drive, Cambridge, Mass. 02140 USA (www.cambridgesoft.com). It will be appreciated by those skilled in the art that in certain instances this program will name a structurally depicted compound as a tautomer of that compound. It is to be understood that any reference to a named compound or a structurally depicted compound is intended to encompass all tautomers of such compounds and any mixtures of tautomers thereof.

In the following experimental descriptions, the following abbreviations may be used:

| Abbreviation | Meaning |
|---|---|
| AcOH | acetic acid |
| aq | aqueous |
| brine | saturated aqueous sodium chloride |
| CH$_2$Cl$_2$ or DCM | methylene chloride |
| CH$_3$CN or MeCN | acetonitrile |
| CH$_3$NH$_2$ | methylamine |
| d | day |
| DCE | 1,2-dichloroethane |
| DMAP | 4-dimethylaminopyridine |
| DMF | N,N-dimethylformamide |
| DMSO | dimethylsulfoxide |
| EDC | 1-ethyl-3-(3-dimethylaminopropyl) carbodiimide |
| equiv | equivalents |
| Et | ethyl |
| Et$_3$N or TEA | triethylamine |
| Et$_2$O | diethyl ether |
| EtOAc | ethyl acetate |
| h, hr(s) | hour(s) |
| HATU | O-(7-Azabenzotriazol-1yl)-N,N,N',N'-tetramethylyronium hexafluorophosphate |
| HCl | hydrochloric acid |
| ICl | iodine monochloride |
| i-Pr$_2$NEt | N',N'-diisopropylethylamine |
| KOt-Bu | potassium tert-butoxide |
| LCMS | liquid chromatography-mass spectroscopy |
| LiHDMS | lithium hexamethyldisilazide |
| Me | methyl |
| MeOH or CH$_3$OH | methanol |
| MgSO$_4$ | magnesium sulfate |
| min | minute(s) |
| MS | mass spectrum |
| μw | microwave |
| Na$_2$CO$_3$ | sodium carbonate |
| NaHCO$_3$ | sodium bicarbonate |
| NaOH | sodium hydroxide |
| Na$_2$SO$_4$ | sodium sulfate |
| N$_2$H$_2$ | hydrazine |
| NH$_4$Cl | ammonium chloride |
| NiCl$_2$•6H$_2$O | nickel (II) chloride hexahydrate |
| NMP | N-methyl-2-pyrrolidone |
| Ph | phenyl |
| POCl$_3$ | phosphoryl chloride |
| rt | room temperature |
| satd. | saturated |
| SPE | solid phase extraction |
| TFA | trifluoroacetic acid |
| THF | tetrahydrofuran |
| t$_R$ | retention time |

Preparation 1

N-(6-(tert-Butylthio)-7-methoxyquinazolin-4-yl)benzo[d]thiazol-5-amine

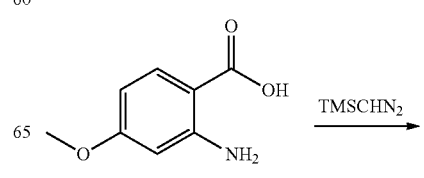

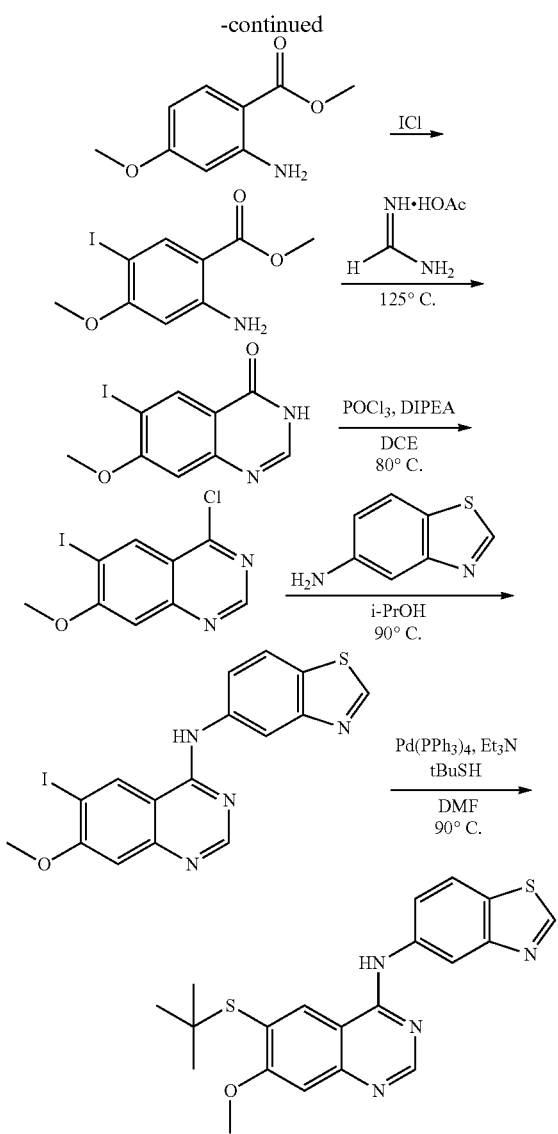

washed with water and dried under vacuum (50° C.) to afford 2.1 g of the title compound (96% pure). MS: m/z: 303 [M+H]$^+$.

Step 4. 4-chloro-6-iodo-7-(methyloxy)quinazoline: 6-Iodo-7-(methyloxy)-4(1H)-quinazolinone (2.0 g, 6.6 mmol), POCl$_3$ (3.1 mL, 33.1 mmol) and DIPEA (6.9 mL, 40 mmol) were combined in DCE (50 mL) in a round bottom flask. The reaction mixture was heated at 80° C. for 5 h, followed by heating at 70° C. overnight. The reaction mixture was allowed to cool to rt. A yellow solid was precipitated out. The solid was filtered. The solution was concentrated and neutralized with satd. NaHCO$_3$, extracted with CH$_2$Cl$_2$ and dried over Na$_2$SO$_4$. The mixture was filtered, and the solvent was removed in vacuo. Solid portions were combined to obtain 2.0 g of the title compound (88%, 93% pure)). MS: m/z: 321 [M+H]$^+$.

Step 5. N-1,3-benzothiazol-5-yl-6-iodo-7-(methyloxy)-4-quinazolinamine: To a solution of 4-chloro-6-iodo-7-(methyloxy)quinazoline (2.0 g, 5.4 mmol) in 1-propanol (30 mL) was added 1,3-benzothiazol-5-amine (1.2 g, 8.1 mmol). The suspension was heated in oil bath at 90° C. (preheated). The reaction mixture was stirred at this temperature for 30 min. A yellow solid precipitated out as the reaction mixture was allowed to cool to rt. The solid was filtered, washed with toluene and dried to provide 1.3 g of the title compound (55.2%, 99% pure). MS: m/z: 435 [M+H]$^+$.

Step 6. N-(6-(tert-butylthio)-7-methoxyquinazolin-4-yl) benzo[d]thiazol-5-amine: To a solution of N-1,3-benzothiazol-5-yl-6-iodo-7-(methyloxy)-4-quinazolinamine (2.1 g, 4.5 mmol), 2-methyl-2-propanethiol (483 mg, 5.35 mmol), Et$_3$N (1.9 mL, 13.4 mmol) in DMF (5 mL) was added Pd(Ph$_3$P)$_4$ (516 mg, 0.45 mmol). The reaction mixture was stirred at 90-100° C. for 1 h. Most of DMF was removed in vacuo. The crude material was triturated with MeOH. The red solid was filtered and washed with Et$_2$O to provide 1.7 g of the title compound as an off white solid (92%, 96% pure). MS: m/z: 397 [M+H]$^+$.

Preparation 2

N-(6-(tert-Butylsulfonyl)-7-methoxyquinazolin-4-yl) benzo[d]thiazol-5-amine

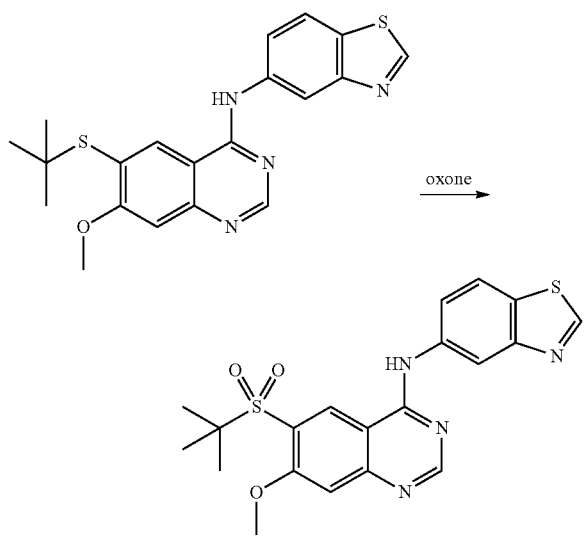

Step 1. Methyl 2-amino-4-methoxybenzoate: To a solution of 2-amino-4-(methyloxy) benzoic acid (5 g, 30 mmol) in MeOH (30 mL) and toluene (60 mL) was added trimethylsilyldiazomethane (30 mL, 60 mmol). The reaction mixture was stirred at 0° C. for 1 h. The reaction mixture was allowed to warm to rt and solvent was removed in vacuo. The crude material was purified by column chromatography (0 to 15% EtOAc/hexanes) to provide 4.2 g of the title compound (74%). MS: m/z: 182 [M+H]$^+$.

Step 2. Methyl 2-amino-5-iodo-4-methoxybenzoate: Methyl 2-amino-4-(methyloxy) benzoate (3.78 g, 20.86 mmol) was dissolved in 25 mL of water, 15 mL of ethanol and 2.2 mL of concentrated HCl. A solution of ICl (1.1 mL, 21.9 mmol) in 3.8 mL concentrated HCl and 14 mL of water at 5° C. was added to the aniline solution. The reaction was stirred overnight and was then filtered to obtain 6.9 g of a light brown solid. MS: m/z: 308 [M+H]$^+$ Step 3. 6-iodo-7-methoxyquinazolin-4(1H)-one: A solution of methyl 2-amino-5-iodo-4-(methyloxy)benzoate (2 g, 6.5 mmol) and imidoformamide (2.0 g, 19.5 mmol) in 2-methoxyethanol (15 mL) was stirred at 125° C. for 6 h. The solvent was removed in vacuo, and the residue was suspended in water and the solid was collected by filtration, To a solution of N-(6-(tert-butylthio)-7-methoxyquinazolin-4-yl)benzo[d]thiazol-5-amine (1.0 g, 2.5 mmol) in THF (20 mL) and water (2 mL) was added oxone (3.1 g, 5.0 mmol). The reaction mixture was stirred at rt for 8 h. Satd. aq. NaHCO$_3$ was added to the reaction mixture to adjust to pH~7. The mixture was extracted with EtOAc (100 mL×2) and CH$_2$Cl$_2$ (100 mL×2), dried over Na$_2$SO$_4$, and filtered. The solvent was removed in vacuo and crude material was purified by column chromatography (0 to 8% MeOH/CH$_2$Cl$_2$) to provide 530 mg of the title compound (43.6%, 89% pure). MS: m/z: 429 [M+H]$^+$.

$^1$H NMR of N-(6-(tert-butyl sulfonyl)-7-methoxyquinazolin-4-yl)benzo[d]thiazol-5-amine: (400 MHz, DMSO-d$_6$) δ 1.34 (s, 9 H), 4.01 (s, 3 H), 7.40 (s, 1 H), 7.89 (dd, J=8.80, 1.78 Hz, 1 H), 8.17 (d, J=8.80 Hz, 1 H), 8.59 (d, J=1.78 Hz, 1 H), 8.64 (s, 1 H), 9.14 (s, 1 H), 9.42 (s, 1 H), 10.55 (s, 1 H).

Preparation 3

4-(Benzo[d]thiazol-5-ylamino)-6-(tert-butylsulfonyl)quinazolin-7-ol

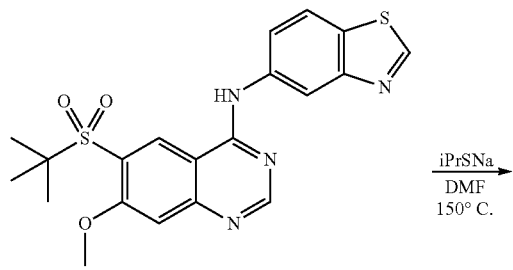

To a solution of N-(6-(tert-butylsulfonyl)-7-methoxyquinazolin-4-yl)benzo[d]thiazol-5-amine (2.0 g, 4.7 mmol) in DMF (30 mL) was added sodium isopropylthiolate (2.7 g, 28.0 mmol), and the solution was stirred at 150° C. for 1 h. Solvent was removed in vacuo. 1 N aq. HCl was added to reaction mixture to neutralize to pH=6. A yellow solid precipitated out, which was filtered and purified by column chromatography (0 to 5% MeOH/CH$_2$Cl$_2$) to provide 1.5 g of the title compound (65.9%, 85% pure). MS: m/z: 415 [M+H]$^+$.

$^1$H NMR of 4-(benzo[d]thiazol-5-ylamino)-6-(tert-butylsulfonyl)quinazolin-7-ol: (400 MHz, DMSO-d$_6$) δ 1.15-1.46 (s, 9 H), 7.21 (s, 1 H), 7.89 (dd, J=8.72, 1.78 Hz, 1 H), 8.16 (d, J=8.72 Hz, 1 H), 8.55 (s, 1 H), 8.58 (d, J=1.78 Hz, 1 H), 9.07 (s, 1 H), 9.42 (s, 1 H), 10.47 (s, 1 H), 11.45 (br. s., 1 H).

Preparation 4

2-((4-(Benzo[d]thiazol-5-ylamino)-6-(tert-butyl sulfonyl)quinazolin-7-yl)oxy)ethanol

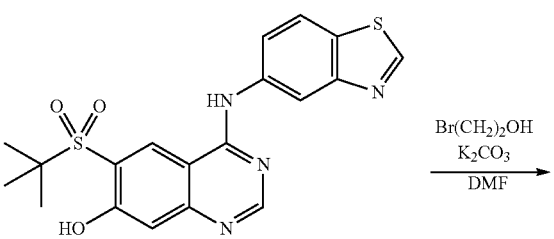

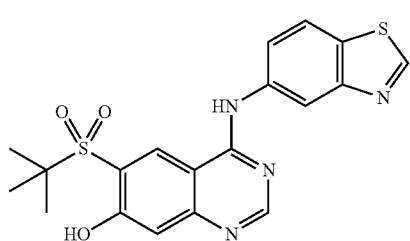

4-(Benzo[d]thiazol-5-ylamino)-6-(tert-butylsulfonyl)quinazolin-7-ol (8.0 g, 19.3 mmol) and K$_2$CO$_3$ (5.9 g, 42.5 mmol) were dissolved in 98 ml DMF and stirred 2 min before adding 2-bromoethanol (5.1 mL, 72.4 mmol). The mixture was heated for 3 h at 70° C., and then cooled to rt and stirred for 18 h. Water (300 mL) was added, and the resulting solid was filtered and washed with water. The wet cake was slurried again in water and filtered to give a tan solid. The solid was dissolved in hot EtOAc/MeOH (150 mL/50 mL) and cooled to rt to give a white solid precipitate which was filtered and dried under vacuum to give the product as a white solid (2.4 g). The resulting filtrate was evaporated to dryness, triturated with EtOAc, filtered, and dried to give a light brown solid (3.1 g). The solids were combined (5.5 g, 62% yield). Several batches of this material were combined to give 15 g of input material. To this solid was added water (150 mL). The mixture was sonicated, and stirred for 15 min at rt. The solid was filtered and dried under vacuum at 70° C. for 3 days to give the title compound as a solid (14.8 g, 98% recovery). MS: m/z: 459 [M+H]$^+$; $^1$H NMR (400 MHz, DMSO-d$_6$) δ 1.36 (s, 9 H), 3.81 (q, J=4.80 Hz, 2 H), 4.28 (t, J=4.80 Hz, 2 H), 4.81 (t, J=4.80 Hz, 1 H), 7.41 (s, 1 H), 7.89 (d, J=8.40 Hz, 1 H), 8.17 (d, J=8.40 Hz, 1 H), 8.58 (s, 1 H), 8.63 (s, 1 H), 9.14 (s, 1 H), 9.42 (s, 1 H), 10.55 (s, 1 H).

Example 1

2-((4-(Benzo[d]thiazol-5-ylamino)-6-(tert-butylsulfonyl)quinazolin-7-yl)oxy)ethyl dihydrogen phosphate

Example 2

2-((4-(Benzo[d]thiazol-5-ylamino)-6-(tert-butylsulfonyl)quinazolin-7-yl)oxy)ethyl disodium phosphate

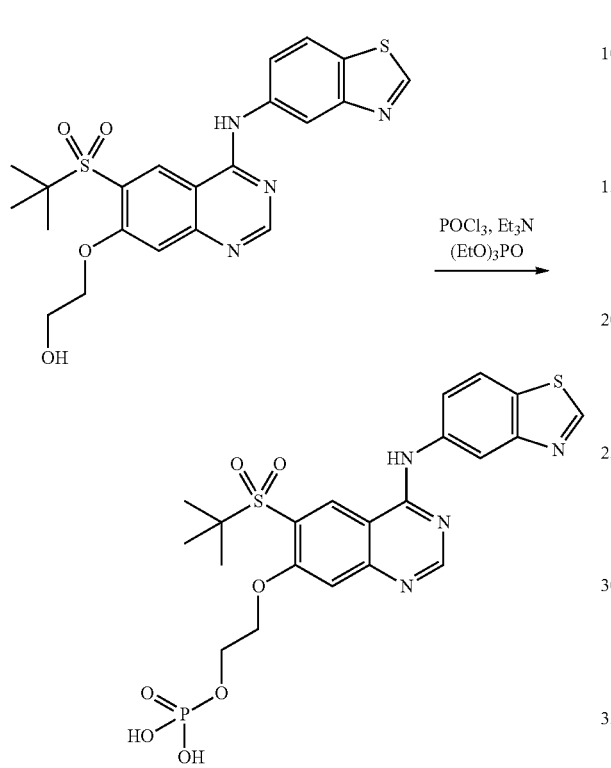

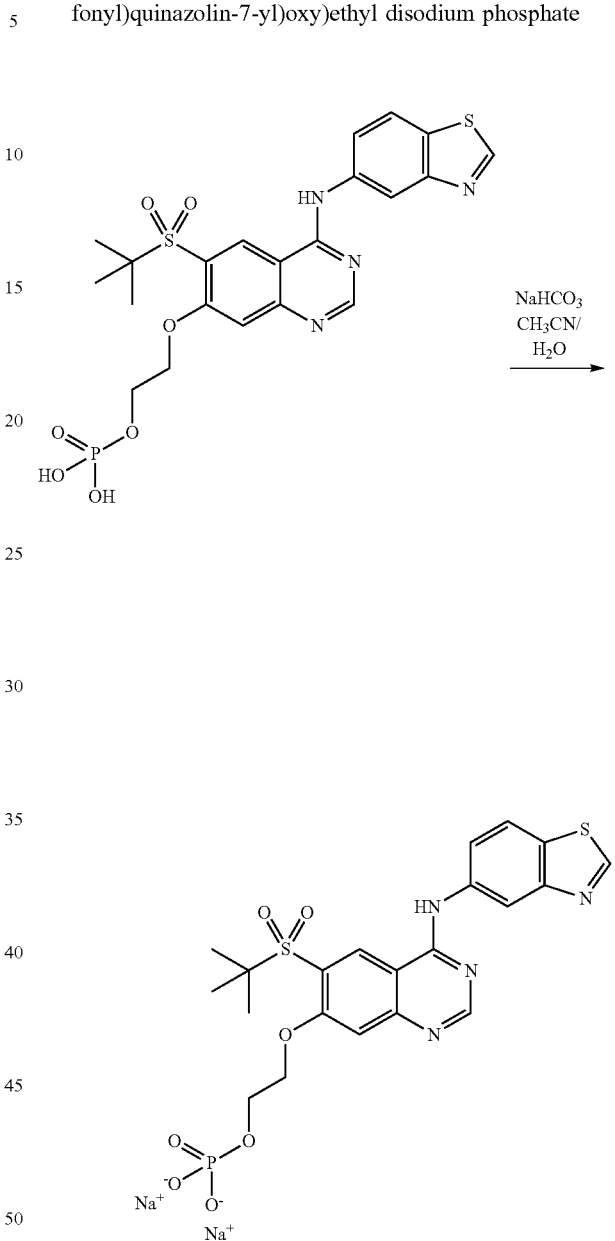

2-((4-(Benzo[d]thiazol-5-ylamino)-6-(tert-butylsulfonyl)quinazolin-7-yl)oxy)ethanol (4 g, 8.72 mmol) and Et$_3$N (1.824 mL, 13.08 mmol) were suspended (with heat gun to warm to dissolve as much as possible, not entirely soluble at this concentration) in triethylphosphate (40 mL) and cooled to 0° C. POCl$_3$ (1.220 mL, 13.08 mmol) was added dropwise slowly at 0° C. with vigorous stirring. The reaction was stirred at 0° C. for 1 hr until complete. The reaction was quenched with water (4 mL) at 0° C. over 10 min, suspended in DMSO-CH$_3$CN-50 mM sodium ammonium phosphate (pH=7) (ratio 1:1:8), then adjusted pH to 7 with NH$_4$OH to give complete solution, and purified by preparatory C18 HPLC (Luna C18, 10μ, 101×250 mm column, 500 mL/min) using gradient 15-21% of CH$_3$CN in 50 mM sodium ammonium phosphate (pH=7) buffer. The fractions containing the desired product (from multiple runs) were combined, adjusted pH to 3.6 with formic acid, and concentrated to 300 mL to give a yellow suspension. The suspension was readjusted pH to 3.6, chilled for 2 h in an ice bath; filtered off product, washed with 50 mL cold water and dried at 40° C. for 18 h on high vacuum to give a yellow solid, 2-((4-(benzo[d]thiazol-5-ylamino)-6-(tert-butylsulfonyl)quinazolin-7-yl)oxy)ethyl dihydrogen phosphate (76% overall yield). $^1$H NMR (400 MHz, DMSO-d$_6$) δ ppm 1.36 (s, 9 H) 4.16-4.28 (m, 3 H) 4.45 (t, J=4.55 Hz, 2 H) 7.43 (s, 1 H) 7.89 (dd, J=8.72, 1.64 Hz, 1 H) 8.17 (d, J=8.59 Hz, 1 H) 8.58 (d, J=1.52 Hz, 1 H) 8.64 (s, 1 H) 9.15 (s, 1 H) 9.42 (s, 1 H) 10.58 (br. s., 1 H); MS (m/z) 539 (M+H$^+$).

2-((4-(Benzo[d]thiazol-5-ylamino)-6-(tert-butylsulfonyl)quinazolin-7-yl)oxy)ethyl dihydrogen phosphate (95 mg, 0.176 mmol) was suspended in CH$_3$CN (2 mL) and water (2 mL), a solution of sodium bicarbonate (29.6 mg, 0.353 mmol) in water (1 mL) was added to give a clear solution which was concentrated to dryness on a rotary evaporator. The resultant residue was triturated with CH$_3$CN and evaporated to dryness on a rotary evaporator to give a white solid, 2-((4-(benzo[d]thiazol-5-ylamino)-6-(tert-butylsulfonyl)quinazolin-7-yl)oxy)ethyl disodium phosphate (103 mg, 100%). $^1$H NMR (400 MHz, D$_2$O) δ ppm 1.15 (s, 9 H) 3.94 (d, J=18.95 Hz, 4 H) 6.31 (s, 1 H) 6.82-7.02 (m, 2 H) 7.37 (br. s., 1 H) 7.76 (s, 1 H) 7.90 (s, 1 H) 8.70 (s, 1 H); MS (m/z) 539 (M−2Na$^+$+3H$^+$).

Example 3

Calcium (I) 2-((4-(benzo[d]thiazol-5-ylamino)-6-(tert-butylsulfonyl)quinazolin-7-yl)oxy)ethyl hydrogen phosphate trihydrate

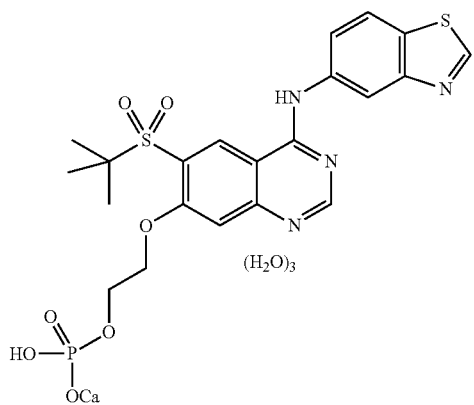

Acetonitrile (11.0 mL) was added to 2-((4-(benzo[d]thiazol-5-ylamino)-6-(tert-butylsulfonyl)quinazolin-7-yl)oxy)ethyl dihydrogen phosphate, (407.1 mg). The suspension was heated to 40° C. and Ca(OAc)$_2$ (0.5M solution in water, 0.5 equivalents) was added in 3 equal portions (10 minutes apart) followed by seeding. The temperature of the suspension was then cycled between 40° C. and 5° C. for ~20 hours. The crystalline solids were isolated by vacuum-filtration under a nitrogen tent. The yield of the filtered solids was 90.1% (411.5 mg). The PXRD pattern of FIG. 1 was obtained after vacuum drying the solids at 40° C. for 4 hours. Stoichiometry of the hemi-calcium salt was confirmed to be 1:0.5 (API: CI) by ICP-AES (3.8%, theoretical for hemi-Ca salt: 3.3%).

Seed crystals of this hydrated form of the hemi-calcium salt were obtained from an analogous procedure conducted on a small scale, absent seeding.

Example 4

2-((4-(Benzo[d]thiazol-5-ylamino)-6-(tert-butylsulfonyl)quinazolin-7-yl)oxy)ethyl dihydrogen phosphate hydrochloride monohydrate

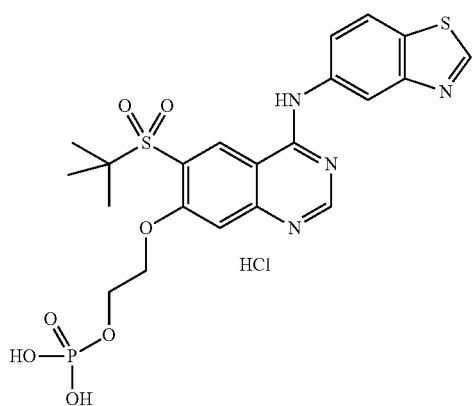 [SMILES: CC(C)(C)S(=O)(=O)c1cc2c(Nc3ccc4scnc4c3)ncnc2cc1OCCOP(=O)(O)O ; Cl]

THF (11.0 mL) was added to 2-((4-(benzo[d]thiazol-5-ylamino)-6-(tert-butylsulfonyl)quinazolin-7-yl)oxy)ethyl dihydrogen phosphate (401.0 mg). The suspension was heated to 40° C. and HCl acid (5M solution in water, 1.0 equivalent) was added in 3 equal portions (10 minutes apart) followed by seeding. The temperature of the suspension was then cycled between 40° C. and 5° C. for ~20 hours. The crystalline solids were isolated by vacuum-filtration under a nitrogen tent. The yield of the filtered solids was 85.9% (379.4 mg). The PXRD pattern of FIG. 2 was obtained after vacuum drying the solids at 40° C. for 4 hours. Stoichiometry of this HCl salt was confirmed to be 1:1 (API:CI) by ion chromatography for chloride content (5.99±0.42%, theoretical for HCl salt: 6.15%).

Seed crystals of this hydrated form of the HCl salt were obtained from an analogous procedure conducted on a small scale, absent seeding.

Example 5

(S)-2-((4-(Benzo[d]thiazol-5-ylamino)-6-(tert-butylsulfonyl)quinazolin-7-yl)oxy)ethyl 2-amino-3-methylbutanoate dihydrochloride a) (S)-2-((4-(benzo[d]thiazol-5-ylamino)-6-(tert-butylsulfonyl)quinazolin-7-yl)oxy)ethyl 2-((tert-butoxycarbonyl)amino)-3-methylbutanoate

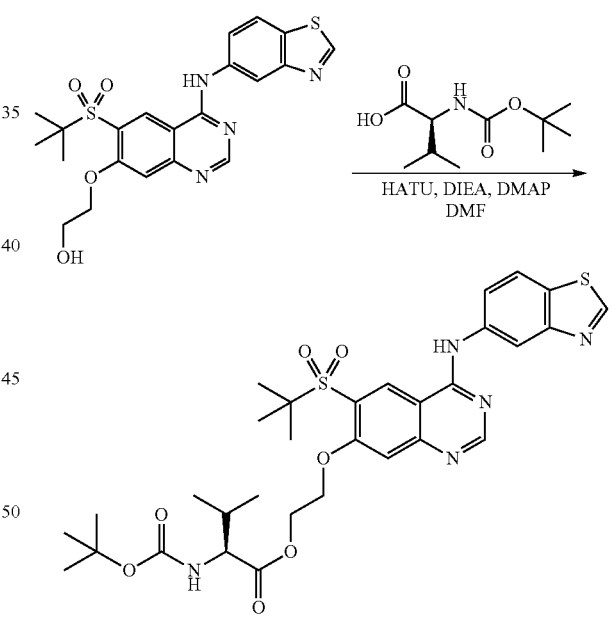

(S)-2-((tert-Butoxycarbonyl)amino)-3-methylbutanoic acid (171 mg, 0.785 mmol) and HATU (498 mg, 1.308 mmol) were dissolved in DMF (4 mL) at rt, i-Pr$_2$NEt (0.229 mL, 1.308 mmol) was added, stirring was continued for 15 min followed by the addition of 2-((4-(benzo[d]thiazol-5-ylamino)-6-(tert-butylsulfonyl)quinazolin-7-yl)oxy)ethanol (300 mg, 0.654 mmol) and DMAP (15.99 mg, 0.13 mmol). The reaction mixture was stirred for 16 hrs at rt, diluted with EtOAc (100 ml), washed with water, brine, dried over MgSO$_4$, and concentrated. The residue was purified on silica gel (40 g, 5% MeOH/DCM) to give (S)-2-((4-(benzo[d]thiazol-5-ylamino)-6-(tert-butylsulfonyl)quinazolin-7-yl)

oxy)ethyl 2-((tert-butoxycarbonyl)amino)-3-methylbutanoate (387 mg, 90%). ¹H NMR (400 MHz, DMSO-d₆) δ ppm 0.87 (t, 6 H) 1.36 (s, 9 H) 1.38 (s, 9 H) 2.03-2.14 (m, 1 H) 3.92 (dd, J=8.08, 6.06 Hz, 1 H) 4.47 (d, J=10.86 Hz, 4 H) 7.14 (d, J=8.34 Hz, 1 H) 7.44 (s, 1 H) 7.89 (dd, J=8.59, 2.02 Hz, 1 H) 8.17 (d, J=8.59 Hz, 1 H) 8.58 (d, J=2.02 Hz, 1 H) 8.64 (s, 1 H) 9.16 (s, 1 H) 9.43 (s, 1 H) 10.57 (s, 1 H); MS (m/z) 658 (M+H⁺).

b) (S)-2-((4-(benzo[d]thiazol-5-ylamino)-6-(tert-butylsulfonyl)quinazolin-7-yl)oxy)ethyl 2-amino-3-methylbutanoate dihydrochloride

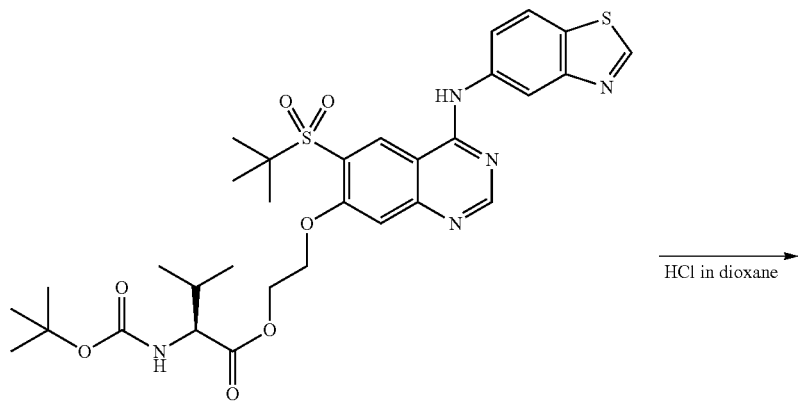

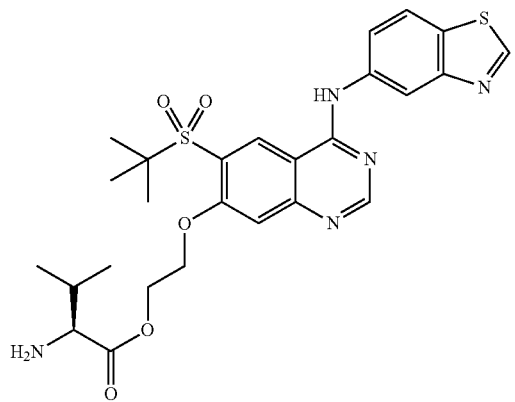

HCl in 1,4-dioxane (4.33 mL, 17.33 mmol) was added to a vial containing (S)-2-((4-(benzo[d]thiazol-5-ylamino)-6-(tert-butylsulfonyl)quinazolin-7-yl)oxy)ethyl 2-((tert-butoxy carbonyl)amino)-3-methylbutanoate (380 mg, 0.578 mmol), the suspension was stirred at rt for 1 hr, concentrated, the solid was collected by filtration, washed with EtOAc, and dried under high vacuum for 16 hrs to give an off-white solid, (5)-2-((4-(benzo[d]thiazol-5-ylamino)-6-(tert-butylsulfonyl)quinazolin-7-yl)oxy)ethyl 2-amino-3-methylbutanoate dihydrochloride (326 mg, 89%). ¹H NMR (400 MHz, DMSO-d₆) δ ppm 0.99 (d, J=7.07 Hz, 6 H) 1.37 (s, 9 H) 2.26 (dd, 1 H) 3.91 (d, J=5.31 Hz, 1 H) 4.60 (d, J=11.87 Hz, 4 H) 7.71 (s, 1 H) 7.78 (dd, J=8.72, 1.64 Hz, 1 H) 8.30 (d, J=8.59 Hz, 1 H) 8.44 (d, J=1.77 Hz, 1 H) 8.56 (br. s., 3 H) 8.95 (s, 1 H) 9.34 (s, 1 H) 9.50 (s, 1 H) 12.09 (br. s., 1H); MS (m/z) 558 (M+H⁺).

The following compound was prepared in the same manner using (R)-2-((tert-butoxy carbonyl)amino)-3-methylbutanoic acid

Example 6

(R)-2-((4-(Benzo[d]thiazol-5-ylamino)-6-(tert-butylsulfonyl)quinazolin-7-yl)oxy)ethyl 2-amino-3-methylbutanoate, dihydrochloride

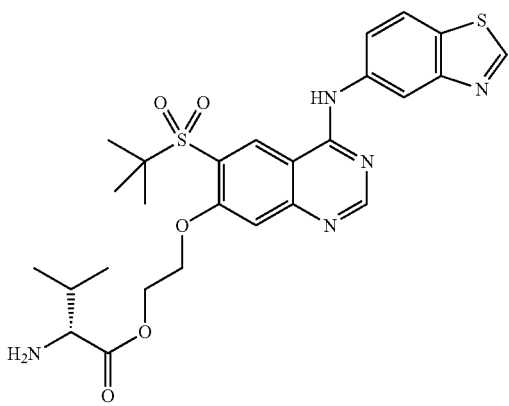 [SMILES: CC(C)[C@@H](N)C(=O)OCCOc1cc2ncnc(Nc3ccc4scnc4c3)c2cc1S(=O)(=O)C(C)(C)C]

$^1$H NMR (400 MHz, DMSO-d$_6$) δ ppm 0.99 (d, 6 H) 1.37 (s, 9 H) 2.21-2.32 (m, 1 H) 3.90 (d, J=4.80 Hz, 1 H) 4.48-4.69 (m, 4 H) 7.69 (s, 1 H) 7.80 (dd, J=8.72, 1.89 Hz, 1 H) 8.28 (d, J=8.59 Hz, 1 H) 8.46 (d, J=2.02 Hz, 1 H) 8.58 (d, J=3.79 Hz, 3 H) 8.91 (s, 1 H) 9.32 (s, 1 H) 9.49 (s, 1 H) 11.88 (br. s., 2 H); MS (m/z) 558 (M+H$^+$).

Example 7

(2S,3S)-2-((4-(Benzo[d]thiazol-5-ylamino)-6-(tert-butylsulfonyl)quinazolin-7-yl)oxy)ethyl 2-amino-3-methylpentanoate

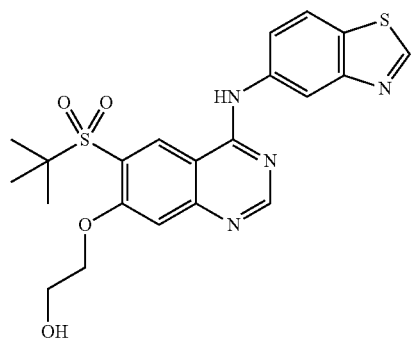

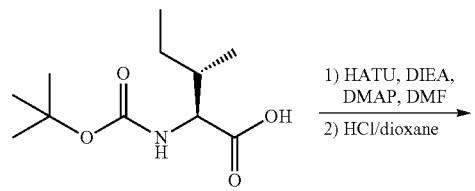

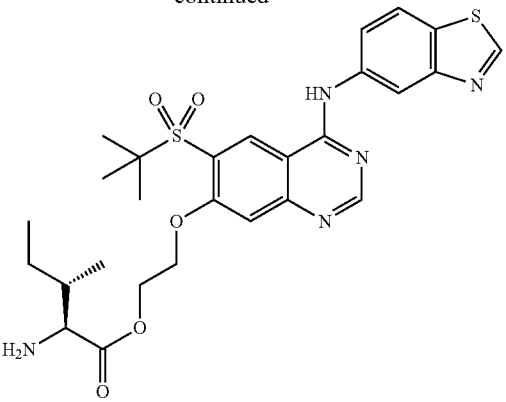

(2S,3S)-2-((tert-Butoxycarbonyl)amino)-3-methylpentanoic acid (60.5 mg, 0.262 mmol) and HATU (166 mg, 0.436 mmol) were dissolved in DMF (2 mL) and cooled at 23° C., DIEA (0.076 mL, 0.436 mmol) and DMAP (5.33 mg, 0.044 mmol) were added, stirring was continued for 30 min followed by addition of 2-((4-(benzo[d]thiazol-5-ylamino)-6-(tert-butylsulfonyl)quinazolin-7-yl)oxy)ethanol (100 mg, 0.218 mmol). The reaction mixture was stirred for 3 days at rt, then heated at 50° C. for 20 hrs, reaction was not complete.

A solution of (2S,3S)-2-((tert-butoxycarbonyl)amino)-3-methylpentanoic acid (121 mg, 0.52 mmol) and HATU (332 mg, 0.87 mmol) and DIEA (0.15 mL, 0.87 mmol) in DMF (1 ml) was prepared and stirred for 15 min before it was added to the above reaction mixture. The resulting reaction mixture was heated at 50° C. for 4 hrs, purified on Gilson HPLC (100×150 mm RP Sunfire column) using 20-70% ACN/water/TFA (0.05%). The fractions containing the desired product were combined, concentrated on rotovap. The residue was dissolved in dioxane (1 ml), then HCl (1 ml, 4M in dioxane) was added at rt, and the resulting mixture was stirred for 1 hr until all starting material converted to desired product. The reaction mixture was concentrated, partitioned between EtOAc and aqueous sodium bicarbonate, the organic layer was separated, washed with brine, dried (MgSO$_4$), and concentrated to give a white solid (2S,3S)-2-((4-(benzo[d]thiazol-5-ylamino)-6-(tert-butylsulfonyl)quinazolin-7-yl)oxy)ethyl 2-amino-3-methylpentanoate (74 mg, 0.126 mmol, 57.6% yield). $^1$H NMR (400 MHz, DMSO-d$_6$) δ ppm 0.78-0.83 (m, 3 H) 0.85 (d, J=6.82 Hz, 3H) 1.05-1.21 (m, 1 H) 1.35 (s, 9 H) 1.43 (ddd, J=13.45, 7.52, 4.29 Hz, 1 H) 1.57-1.70 (m, 1 H) 3.15-3.23 (m, 1 H) 4.34-4.57 (m, 4 H) 7.44 (s, 1 H) 7.89 (dd, J=8.72, 1.89 Hz, 1 H) 8.17 (d, J=8.59 Hz, 1 H) 8.58 (d, J=1.77 Hz, 1 H) 8.64 (s, 1 H) 9.15 (s, 1 H) 9.42 (s, 1 H) 10.56 (s, 1 H); MS (m/z) 572 (M+H$^+$).

Example 8

Biological Assays

In vivo Assay (I)

The efficacy of RIP2 inhibitors may be evaluated in vivo in rodents. Intraperitoneal (i.p.) or intravenous (i.v.) administration of L18-MDP in mice has been shown to induce an inflammatory response through activation of the NOD2 signaling pathway (Rosenweig, H. L., et al. 2008. Journal of Leukocyte Biology 84:529-536). The level of the inflammatory response in the L18-MDP treated mice/rats is monitored using conventional techniques by measuring increases in cytokine levels (IL8, TNFα, IL6 and IL-1β) in serum and/or peritoneal lavage fluid and by measuring neutrophil influx into the peritoneal space (when L18-MDP is dosed i.p.). Inhibition of the L18-MDP induced inflammatory response in treated rodents may be shown by orally pre-dosing with test compounds, then measuring and comparing cytokine levels (IL8, TNFα, IL6 and IL-1β) in serum and/or peritoneal lavage fluid and neutrophil influx into the peritoneal space (when L18-MDP is dosed i.p.) using conventional techniques.

Figure 3:
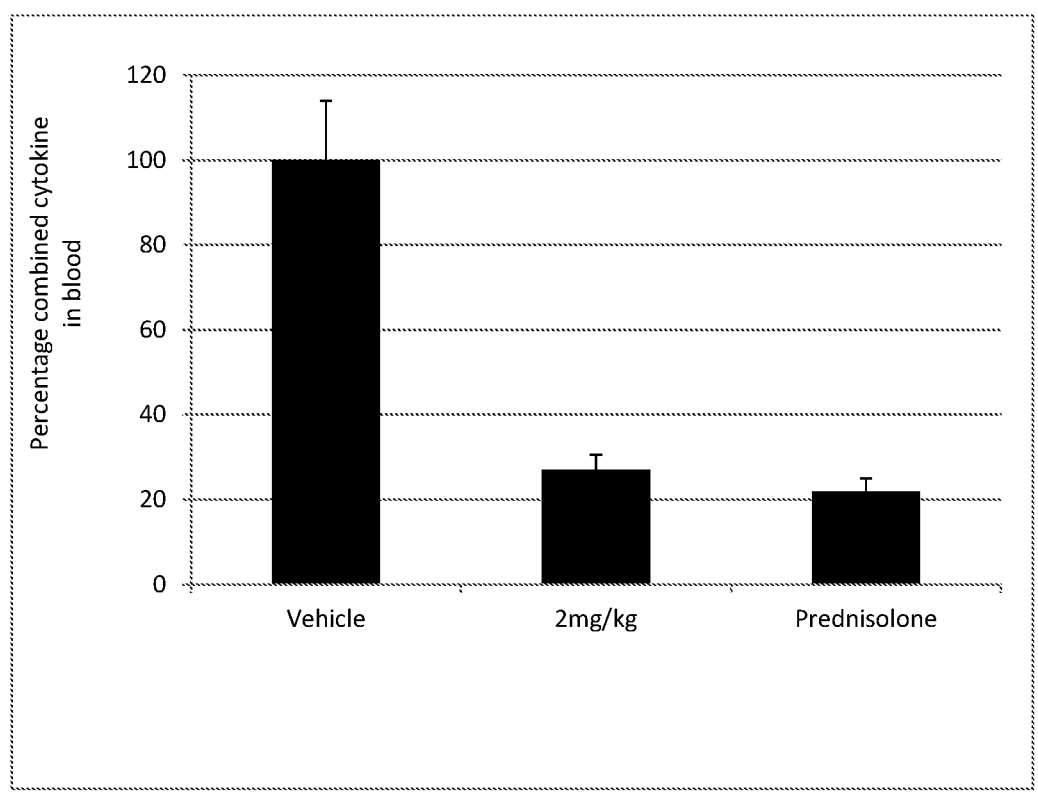
FIG. 3 shows the combined cytokine response in rat whole blood samples obtained after pre-dosing rats with the compound 2-((4-(benzo[d]thiazol-5-ylamino)-6-(tert-butylsulfonyl)quinazolin-7-yl)oxy)ethanol, or prednisolone, followed by dosing with L18-MDP.

Rats were orally pre-dosed with the compound, 2-((4-(benzo[d]thiazol-5-ylamino)-6-(tert-butylsulfonyl)quinazolin-7-yl)oxy)ethanol, at a dose of 2 mg/kg (8 rats) and with prednisolone (8 rats, used as a positive control), followed by dosing with L18-MDP (50 µg/rat) 0.25 h/min after pre-dosing. Combined cytokine levels (IL8, TNFα, IL6 and IL-1β) in whole blood samples taken from the rats in this study were measured using an antibody based detection (Meso-Scale Discovery platform). The combined cytokine response was calculated as the averaged response for the 4 cytokines measured relative to the response observed in the vehicle-treated mice, and are depicted in FIG. 3 as the mean±standard error of the mean (n=8 rats/group).

In vivo Assay (II)

Figure 4:
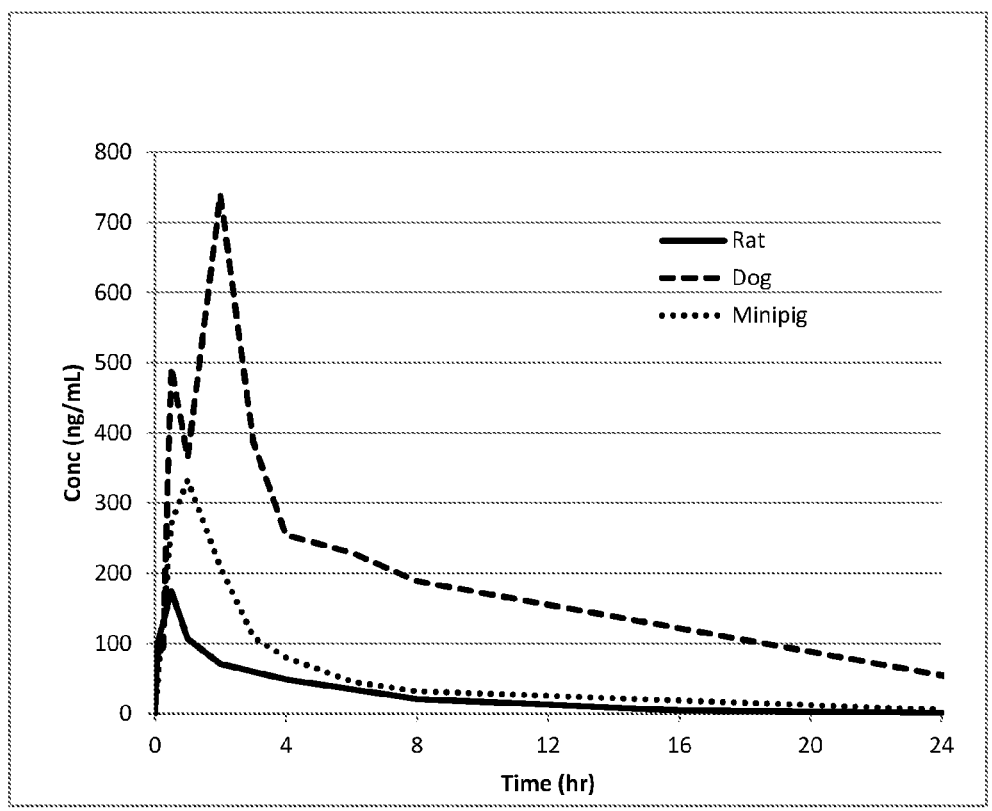
FIG. 4 shows the blood profile of 2-((4-(benzo[d]thiazol-5-ylamino)-6-(tert-butylsulfonyl)quinazolin-7-yl)oxy)ethanol following oral administration of 2-((4-(benzo[d]thiazol-5-ylamino)-6-(tert-butylsulfonyl)quinazolin-7-yl)oxy)ethyl dihydrogen phosphate in rat, dog and minipig.

2-((4-(Benzo[d]thiazol-5-ylamino)-6-(tert-butylsulfonyl)quinazolin-7-yl)oxy)ethyl dihydrogen phosphate was orally administered at a dose equivalent to 2 mg/kg of 2-((4-(benzo[d]thiazol-5-ylamino)-6-(tert-butylsulfonyl)quinazolin-7-yl)oxy)ethanol to a series of test animals. Rats (n=2) and dogs (n=3) were administered 2-((4-(benzo[d]thiazol-5-ylamino)-6-(tert-butylsulfonyl)quinazolin-7-yl)oxy)ethyl dihydrogen phosphate, whereas minipigs (male Göttingen minipigs (n=3)) were administered 2-((4-(benzo[d]thiazol-5-ylamino)-6-(tert-butylsulfonyl)quinazolin-7-yl)oxy)ethyl disodium phosphate. Blood samples were taken from each test animal at intervals between 0 to 24 hrs (25 hrs in dog) after administration. The concentration 2-((4-(benzo[d]thiazol-5-ylamino)-6-(tert-butylsulfonyl)quinazolin-7-yl)oxy)ethanol in each sample was determined by LC/MS. The average blood concentrations of 2-((4-(benzo[d]thiazol-5-ylamino)-6-(tert-butylsulfonyl)quinazolin-7-yl)oxy)ethanol in each test species, following oral administration of 2-((4-(benzo[d]thiazol-5-ylamino)-6-(tert-butylsulfonyl)quinazolin-7-yl)oxy)ethyl dihydrogen phosphate or disodium phosphate are shown in FIG. 4.

The half life ($T_{1/2}$) of 2-((4-(benzo[d]thiazol-5-ylamino)-6-(tert-butylsulfonyl)quinazolin-7-yl)oxy)ethyl dihydrogen phosphate was determined to be 15 min in rat and 5 min in dog. The half life ($T_{112}$) of 2-((4-(benzo[d]thiazol-5-ylamino)-6-(tert-butylsulfonyl)quinazolin-7-yl)oxy)ethyl disodium phosphate was determined to be 26 min in minipig.

Pharmaceutical Compositions

Example A

Tablets are prepared using conventional methods and are formulated as follows:

| Ingredient | Amount per tablet |
| --- | --- |
| Compound | 5 mg |
| Microcrystalline cellulose | 100 mg |
| Lactose | 100 mg |
| Sodium starch glycollate | 30 mg |
| Magnesium stearate | 2 mg |
| Total | 237 mg |

Example B

Capsules are prepared using conventional methods and are formulated as follows:

| Ingredient | Amount per tablet |
| --- | --- |
| Compound | 15 mg |
| Dried starch | 178 mg |
| Magnesium stearate | 2 mg |
| Total | 195 mg |

What is claimed is:
1. A compound which is:

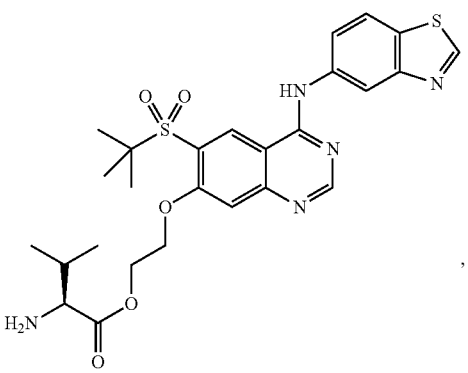 [SMILES: CC(C)[C@H](N)C(=O)OCCOc1cc2ncnc(Nc3ccc4scnc4c3)c2cc1S(=O)(=O)C(C)(C)C]

or a pharmaceutically acceptable salt thereof.

2. A compound which is (S)-2-((4-(benzo[d]thiazol-5-ylamino)-6-(tert-butylsulfonyl)quinazolin-7-yl)oxy)ethyl2-amino-3-methylbutanoate.

3. The compound, or pharmaceutically acceptable salt thereof, according to claim 1, which is the pharmaceutically acceptable salt of said compound.

4. The compound, or pharmaceutically acceptable salt thereof, according to claim 3, wherein the pharmaceutically acceptable salt is a hydrochloride salt.

5. A compound which is (S)-2-((4-(benzo[d]thiazol-5-ylamino)-6-(tert-butylsulfonyl)quinazolin-7-yl)oxy)ethyl2-amino-3-methylbutanoate dihydrochloride.

6. A pharmaceutical composition comprising the compound, or pharmaceutically acceptable salt thereof, according to claim 1, and a pharmaceutically acceptable excipient.

* * * * *